United States Patent [19]
Gonzalez et al.

[11] Patent Number: 6,015,673
[45] Date of Patent: Jan. 18, 2000

[54] CLONING AND EXPRESSION OF CDNA FOR HUMAN DIHYDROPYRIMIDINE DEHYDROGENASE

[75] Inventors: Frank J. Gonzalez; Pedro Fernandez-Salguero, both of Bethesda, Md.

[73] Assignee: The United States of America as represented by the Department of Health and Human Services, Washington, D.C.

[21] Appl. No.: 08/991,942

[22] Filed: Dec. 16, 1997

Related U.S. Application Data

[62] Division of application No. 08/304,309, Sep. 12, 1994, Pat. No. 5,856,454.

[51] Int. Cl.$^7$ .............................. C12Q 1/68; C12P 15/34; C07H 21/04
[52] U.S. Cl. ........................ 435/6; 435/91.2; 536/24.3; 536/24.31; 536/24.32; 536/24.33
[58] Field of Search ..................... 435/6, 91.2; 536/24.3, 536/24.31, 24.32, 24.33

[56] References Cited

PUBLICATIONS

Cheng et al, "Molecular cloning of dihydropyrimidine dehydrogenase", Clin. Pharm. Therap. 55(2):188, Feb. 1994.

Gaedgk et al, "Characterization of the microsomal epoxide hydrolase gene in patients with anticonvulsant adverse drug reactions", Pharmacogenetics 4(3):142–153 Abstract Only, Jun. 1994.

Lu et al, "Dihydropyrimidine dehydrogenase activity in human peripheral blood mononucleasr cells and liver: Population characteristics, newly identified patients and clinical implication in 5–fluorouracil therapy", Cancer Research 53:5433–5438, Nov. 1993.

*Primary Examiner*—Jeffrey Fredman
*Attorney, Agent, or Firm*—Townsend and Townsend and Crew LLP

[57] ABSTRACT

The invention relates to methods and compositions that are useful for detecting deficiencies in dihydropyrimidine dehydrogenase (DPD) levels in mammals including humans. Cancer patients having a DPD deficiency are at risk of a severe toxic reaction to the commonly used anticancer agent 5-fluorouracil (5-FU). Claimed are DPD genes from human and pig, methods for detecting the level of nucleic acids that encode DPD in a patient, and nucleic acids that are useful as probes for this purpose. Also claimed are methods for expressing DPD in heterologous organisms. Expression vectors that employ a DPD nucleic acid as a selectable marker are also claimed. This selectable marker functions in both prokaryotes and eukaryotes.

9 Claims, 11 Drawing Sheets

```
   1 GCTGTCACTT GGCTCTCTGG CTGGAGCTTG AGGACGCAAG GAGGGTTTGT CACTGGCAGA
  61 CTCGAGACTG TAGGCACTGC CATGGCCCCT GTGCTCAGTA AGGACTCGGC GGACATCGAG
 121 AGTATCCTGG CTTTAAATCC TCGAACACAA ACTCATGCAA CTCTGTGTTC CACTTCGGCC
 181 AAGAAATTAG ACAAGAAACA TTGGAAAAGA AATCCTGATA AGAACTGCTT TAATTGTGAG
 241 AAGCTGGAGA ATAATTTTGA TGACATCAAG CACACGACTC TTGGTGAGCG AGGAGCTCTC
 301 CGAGAAGCAA TGAGATGCCT GAAATGTGCA GATGCCCCGT GTCAGAAGAG CTGTCCAACT
 361 AATCTTGATA TTAAATCATT CATCACAAGT ATTGCAAACA AGAACTATTA TGGAGCTGCT
 421 AAGATGATAT TTTCTGACAA CCCACTTGGT CTGACTTGTG GAATGGTATG TCCAACCTCT
 481 GATCTATGTG TAGGTGGATG CAATTTATAT GCCACTGAAG AGGACCCCAT TAATATTGGT
 541 GGATTGCAGC AATTTGCTAC TGAGGTATTC AAAGCAATGA GTATCCCACA GATCAGAAAT
 601 CCTTCGCTGC CTCCCCAGA AAAAATGTCT GAAGCCTATT CTGCAAAGAT TGCTCTTTTT
 661 GGTGCTGGGC CTGCAAGTAT AAGTTGTGCT TCCTTTTTGG CTCGATTGGG GTACTCTGAC
 721 ATCACTATAT TTGAAAAACA AGAATATGTT GGTGGTTTAA GTACTTCTGA AATTCCTCAG
 781 TTCCGGCTGC CGTATGATGT AGTGAATTTT GAGATTGAGC TAATGAAGGA CCTTGGTGTA
 841 AAGATAATTT GCGGTAAAAG CCTTTCAGTG AATGAAATGA CTCTTAGCAC TTTGAAAGAA
 901 AAAGGCTACA AAGCTGCTTT CATTGGAATA GGTTTGCCAG AACCCAATAA AGATGCCATC
 961 TTCCAAGGCC TGACGCAGGA CCAGGGGTTT TATACATCCA AAGACTTTTT GCCACTTGTA
1021 GCCAAAGGCA GTAAAGCAGG AATGTGCGCC TGTCACTCTC CATTGCCATC GATACGGGGA
1081 GTCGTGATTG TACTTGGAGC TGGAGACACT GCCTTCGACT GTGCAACATC TGCTCTACGT
1141 TGTGGAGCTC GCCGAGTGTT CATCGTCTTC AGAAAAGGCT TTGTTAATAT AAGAGCTGTC
1201 CCTGAGGAGA TGGAGCTTGC TAAGGAAGAA AAGTGTGAAT TTCTGCCATT CCTGTCCCCA
1261 CGGAAGGTTA TAGTAAAAGG TGGGAGAATT GTTGCTATGC AGTTTGTTCG GACAGAGCAA
1321 GATGAAACTG GAAAATGGAA TGAAGATGAA GATCAGATGG TCCATCTGAA AGCCGATGTG
1381 GTCATCAGTG CCTTTGGTTC AGTTCTGAGT GATCCTAAAG TAAAAGAAGC CTTGAGCCCT
1441 ATAAAATTTA ACAGATGGGG TCTCCCAGAA GTAGATCCAG AAACTATGCA AACTAGTGAA
1501 GCATGGGTAT TTGCAGGTGG TGATGTCGTT GGTTTGGCTA CACACACGA GGAATCGGTG
1561 AATGATGGAA AGCAAGCTTC TTGGTACATT CACAAATACG TACAGTCACA ATATGGAGCT
1621 TCCGTTTCTG CCAAGCCCTG ACTACCCCTC TTTTACACTC CTATTGATCT GGTGGACATT
```

FIG. 1A-1.

```
1681 AGTGTAGAAA TGGCCGGATT GAAGTTTATA AATCCTTTTG GTCTTGCTAG CGCAACTCCA
1741 GCCACCAGCA CATCAATGAT TCGAAGAGCT TTTGAAGCTG GATGGGGTTT TGCCCTCACC
1801 AAAACTTTCT CTCTTGATAA GGACATTGTG ACAAATGTTT CCCCAGAAT CATCCGGGGA
1861 ACCACCTCTG GCCCCATGTA TGGCCCTGGA CAAAGCTCCT TTCTGAATAT TGAGCTCATC
1921 AGTGAGAAAA CGGCTGCATA TTGGTGTCAA AGTGTCACTG AACTAAAGGC TGACTTCCCA
1981 GACAACATTG TGATTGCTAG CATTATGTGC AGTTACAATA AAAATGACTG GACGGAACTT
2041 GCCAAGAAGT CTGAGGATTC TGGAGCAGAT GCCCTGGAGT TAAATTTATC ATGTCCACAT
2101 GGCATGGGAG AAAGAGGAAT GGGCCTGGCC TGTGGGCAGG ATCCAGAGCT GGTGCGGAAC
2161 ATCTGCCGCT GGGTTAGGCA AGCTGTTCAG ATTCCTTTTT TTGCCAAGCT GACCCCAAAT
2221 GTCACTGATA TTGTGAGCAT CGCAAGAGCT GCAAAGGAAG GTGGTGCCAA TGGCGTTACA
2281 GCCACCAACA CTGTCTCAGG TCTGATGGGA TTAAAATCTG ATGGCACACC TTGGCCAGCA
2341 GTGGGATTG CAAAGCGAAC TACATATGGA GGAGTGTCTG GGACAGCAAT CAGACCTATT
2401 GCTTTGAGAG CTGTGACCTC CATTGCTCGT GCTCTGCCTC GATTTCCCAT TTTGGCTACT
2461 GGTGGAATTG ACTCTGCTGA AAGTGGTCTT CAGTTTCTCC ATAGTGGTGC TTCCGTCCTC
2521 CAGTATGCA GTGCCATTCA GAATCAGGAT TTCACTGTGA TCGAAGACTA CTGCACTGGC
2581 CTCAAAGCCC TGCTTTATCT GAAAAGCATT GAAGAACTAC AAGACTGGGA TGGACAGAGT
2641 CCAGCTACTG TGAGTCACCA CCAGTTCCAC CCAGTTCCAC GTATAGCTGA ACTCATGGAC
2701 AAGAAACTGC CAAGTTTTGG ACCTTATCTG GAACAGCGCA AGAAAATCAT AGCAGAAAAC
2761 AAGATTAGAC TGAAAGAACA AAATGTAGCT TTTTCACCAC TTAAGAGAAG CTGTTTTATC
2821 CCCAAAAGGC CTATTCCTAC CATCAAGGAT GTAATAGGAA AAGCACTGCA GTACCCTTGGA
2881 ACATTTGGTG AATTGAGCAA CGTAGAGCAA GTTGTGGCTA TGATTGATGA AGAAATGTGT
2941 ATCAACTGTG GTAAATGCTA CATGACCTGT AATGATTCTG GCTACCAGGC TATACAGTTT
3001 GATCCAGAAA CCCACCTGCC CACCATAACC GACACTTGTA CAGGCTGTAC TCTGTGTCTC
3061 AGTGTTTGCC CTATTGTCGA CTGCATCAAA ATGGTTTCCA GGACAACACC TTATGAACCA
3121 AAGAGAGGCG TACCCTTATC TGTGAATCCG GTGTGTTAAG GTGATTTGTG AAACAGTTGC
3181 TGTGAACTTT CATGTCACCT ACATATGCTT ATCTCTTAAA ATCATGATCC TTGTGTTCAG
3241 CTCTTTCCAA ATTAAAACAA ATATACATTT TCTAAATAAA AATATGTAAT TTCAAAATAC
3301 ATTTGTAAGT GTAAAAAATG TCTCATGTCA ATGACCATTC AATTAGTGGN CATAAAATAG
```

*FIG. 1A-2.*

```
3361 AATAATTCTT TTCTGAGGAT AGTAGTTAAA TAACTGTGTG GCAGTTAATT GGATGTTCAC
3421 TGCCAGTTGT CTTATGTGAA AAATTAACTT TTTGTGTGGC AATTAGTGTG ACAGTTTCCA
3481 AATTGCCCTA TGCTGTGCTC CATATTTGAT TTCTAATTGT AAGTGAAATT AAGCATTTTG
3541 AAACAAAGTA CTCTTTAACA TACAAGAAAA TGTATCCAAG GAAACATTTT ATCAATAAAA
3601 ATTACCTTTA ATTTTAATGC TGTTTCTAAG AAAATGTAGT TAGCTCCATA AAGTACAAAT
3661 GAAGAAAGTC NAAAAATTAT TTGCTATGGC AGGATAAGAA AGCCTAAAAT TGAGTTTGTN
3721 GGACTTTATT AAGTAAAATC CCCTTCGCTG AAATTGCTTA TTTTTGGTGT TGGATAGAGG
3781 ATAGGGAGAA TATTTACTAA CTAAATACCA TTCACTACTC ATGCGTGAGA TGGGTGTACA
3841 AACTCATCCT CTTTTAATGG CATTTCTCTT TAAACTATGT TCCTAACCAA ATGAGATGAT
3901 AGGATAGATC CTGGTTACCA CTCTTTTACT GTGCACATAT GGGCCCCGGA ATTC
```

*FIG. 1B.*

```
   1 TCGACCCCACG CGTCCGCCGG CCGGAGGCGG AGGACGCGGG GAGGGCCCGC CGGTGGGAGA
  61 CTCCAAGCTG TCGGCATCGC CATGGCCCCT GTGCTGAGCA AGGACGTGGC GGACATCGAG
 121 AGTATCCTGG CTTTAAATCC TCGAACACAG TCTCATGCAG CCCTTCATTC CACTTTGGCC
 181 AAGAAATTGG ATAAGAAACA CTGGAAAAGA AATCCCGATA AGAACTGCTT TCATTGCGAG
 241 AAGCTGGAGA ATAATTTTGG TGACATCAAG CACACGACTC TTGGTGAGCG AGGAGCTCTC
 301 CGAGAAGCAA TGAGATGCCT GAAATGTGCC GATGCTCCCT GTCAGAAGAG CTGTCCAACT
 361 CATCTAGATA TCAAATCATT CATCACAAGT ATCTCAAATA AGAACTATTA TGGAGCTGCT
 421 AAGATGATTT TTTCTGACAA CCCTCTTGGT CTGACCTGTG GAATGGTATG TCCAACCTCT
 481 GATCTTTGTG TAGGAGGATG CAATTATATAT GCAACTGAAG AGGGATCAAT TAATATTGGT
 541 GGATTGCAGC AGTTTGCTTC TGAGGTGTTC AAAGCAATGA ATATCCCACA AATCAGGAAT
 601 CCTTGTCTGC CATCCCAAGA GAAAATGCCT GAAGCTTATT CTGCAAAGAT TGCTCTTTTG
 661 GGTGCTGGGC CTGCAAGTAT AAGCTGTGCT TCCTTCTTGG CTCGATTAGG CTACTCTGAC
 721 ATCACTATAT TTGAAAAACA AGAATATGTT GGTGGTTTAA GTACTTCTGA AATCCCTGTA
 781 TTCCGGCTGC CATATGATGT AGTGAATTTT GAGATTGAGC TTATGAAGGA CCTTGGTGTA
 841 AAGATAATTT GTGGTAAAAG CCTTTCAGAG AATGAAATTA CTCTCAACAC TTTAAAAGAA
 901 GAAGGGTATA AAGCTGCTTT CATTGGTATA CCAGGGGTTT AACCCAAAAC GGATGACATC
 961 TTCCAAGGCC TGACACAGGA CCAGGGGTTT TACACATCCA AAGACTTTCT GCCCCTTGTA
1021 GCCAAAAGCA GTAAAGCAGG AATGTGTGCC TGTCACTCTC CATTGCCATC GATACGGGGA
1081 GCCGTGATTG TACTCGGAGC TGGAGACACA GCTTTCGACT GTGCAACATC CGCTTTACGT
1141 TGTGGGAGCCC GCCGAGTGTT CCCTCGTCTTC AGAAAAGGCT TTGTTAATAT AAGAGCTGTC
1201 CCTGAGGAGG TGGAGCTTGC TAAGGAAGAA AAATGTGAAT TTTTGCCTTT CCTGTCCCCA
1261 CGGAAGGTTA TAGTTAAAGG TGGGAGAATT GTTGCCGTGC AATTTGTTCG AACAGAACAA
1321 GATGAAACTG GAAAATGGAA TGAAGATGAA GATCAGATAG TCCATCTGAA GGCTGATGTG
1381 GTCATCAGTG CCTTTGGCTC AGTGCTGAGG GATCCCTAAAG TAAAAGAAGC CTTGAGCCCT
1441 ATAAAATTTA ACAGATGGGA TCTCCCAGAA GTAGATCCAG AAACTATGCA AACCAGTGAA
1501 CCATGGGTGT TTGCAGGTGG TGATATCGTT GGTATGGCTA ACACTACGGT GGAATCCGTA
1561 AATGACGGAA AGCAGGCCTC CTGGTACATT CACAAATATA TCCAGGCCCA ATATGGAGCT
1621 TCAGTTTCTG CCAAGCCCGA ACTGCCCCTG TTTTATACGC CTGTTGACCT GGTGGACATC
```

FIG. 2A-1.

```
1681 AGCGTGGAAA TGGCTGGATT AAAGTTTATA AATCCTTTTG GTCTTGCCAG TGCAGCTCCA
1741 ACTACCAGTT CATCGATGAT TCGAAGAGCT TTTGAAGCTG GATGGGGTTT TGCCCTGACC
1801 AAAACTTTCT CTCTTGATAA GGACATAGTG ACAAATGTCT CACCCAGAAT CGTCCGGGGG
1861 ACTACCTCTG GCCCCATGTA CGGCCCTGGA CAAAGCTCCT TCCTGAATAT TGAGCTCATC
1921 AGTGAAAAAA CAGCTGCATA TTGGTGTCAA AGTGTCACTG AACTAAAAGC TGACTTTCCA
1981 GACAATATTG TGATCGCCAG CATCATGTGT AGTTACAACA AAAATGACTG GATGGAACTC
2041 TCCAGAAAGG CTGAGGCCTC TGGAGCAGAT GCCCTTGGAGT TAAATCTGTC ATGTCCACAC
2101 GGCATGGGAG AAAGAGGAAT GGGCCTGGCT TGTGGGCAGG ATCCAGAGCT GGTGCGGAAC
2161 ATCTGTCGCT GGGTTAGGCA AGCTGTTCAG ATTCCCTTTT TTGCCAAGTT GACCCCAAAC
2221 GTCACTGATA TAGTAAGCAT CGCCAGAGCG GCCAAGGAAG GTGGCGCAGA TGGTGTTACA
2281 GCCACCAACA CGGTCTCAGG TCTCATGGGA TTAAAAGCCG ATGGCACGCC CTGGCCAGCG
2341 GTGGGTGCTG GCAAGCGGAC TACATACGGA GGAGTGTCTG GCACGGCCAT CAGACCAATT
2401 GCTTTGAGAG CTGTGACCAC CATTGCTCGT GCTTTGCCTG GATTTCCCAT TTTGGCTACT
2461 GGTGGAATTG ACTCAGCTGA AAGTGGACTT CAGTTTCTCC ACAGTGGTGC TTCGGTCCTC
2521 CAGGTATGCA GTGCTGTTCA GAATCAGGAT TTCACTGTCA TCCAAGACTA TTGCACTGGC
2581 CTCAAAGCCT TGCTTTATCT GAAAAGCATT GCTTTCCTC AAGGCTGGGA TGGGCAGAGT
2641 CCAGGTACCG AGAGTCACCA GAAGGGGAAA CCAGTTCCTC GTATTGCTGA ACTCATGGA
2701 AAGAAACTGC CAAATTTTGG ACCTTATCTG GAGCAACGCA AGAAAATCAT AGCAGAGGAA
2761 AAGATGAGAC TGAAAGAACA AAATGCAGCT TTTCCACCAC TTGAGAGAAA ACCTTTTATT
2821 CCCAAAAAGC CTATTCCTGC TATTAAGGAT GTAATTGGAA AAGCACTGCA GTACCTTGGA
2881 ACGTTTGGTG AACTGAGCAA CATAGAGCAA GTTGTGGCTG TGATCGATGA AGAAATGTGT
2941 ATCAACTGTG GCAAATGCTA CATGACCTGT AATGACTCTG GCTACCAGGC TATCCAGTTT
3001 GATCCCGAAA CCCACCTGCC CACCGTTACT GACACTTGCA CAGGCTGTAC CCTGTGTCTC
3061 TCCGTCTGCC CTATTATCGA CTGCATCAGA ATGGTTTCCA GGACAACACC TTACGAACCA
3121 AAGAGAGGCT TGCCCCTTGG TGTGAATCCG GTGTGCTGAG GTGATTCGTG GAACAGTTGC
3181 TGTGAACTTT GAGGTCACCC CCATATGCTG TCTTTTTAAT TGTGGTTATT ATACTCAGCT
3241 CTTTCTCAAT GAAAACAAAT ATAATATTTC TAGATAAAAG TTCTAAATAC ATGTCTAAAT
3301 TTTAAAAAAC ATCTACTGCC AGAGCCCGTT CAATTAATGG TGATAAAATA GAATCCTCCT
```

*FIG. 2A-2.*

```
3361 TTTCTGAGGC TAGTTGTTCA ATAACTGCTG CAGTTAATTG GATGTTCTCC ATCAGTTATC
3421 CATTATGAAA AATATTAACT TTTTGGTGG  CAATTCCAA  ATTGCCCTAT GCTGTGCTCT
3481 GTCTTTGATT TCTAATTGTA AGTGAAGTTA AGCATTTTAG AACAAAGTAT AATTTAACTT
3541 TCAAGCAAAT GTTCCAAGG  AAACATTTTA TAATTAAAAA TTACAATTTA ATTTTAACAC
3601 TGTTCCTAAG CAAATGTAAT TAGCTCCATA AAGCTCAAAT GAAGTCAAAT AATTATTTAC
3661 TGTGGCAGGA AAAGAAAGCC AATGAGGGT  TGCAAAACTT CTCTAAGGCC CTTTGGCTGA
3721 AATAACTTCT CTTGGTGCT  ACATACTGAA AGTGACTGTT TAATCATCAT TCATGTCACA
3781 CCGTGCTCCC TCGCCCCTCA GCCTGAGATG GGTCTCCAGA CTCCACCAGT GAATCAGCAT
3841 GACACCTTCT TTAACTGTGT GAGCGACGTT CCTAACAAAG TAAGGTGTGG GGATGAAGCT
3901 CTGGTTAAAG CCACTCTTT  GCTGTGCTCC GATCTGTTCT ATCCGCTTCT GAGAGCAACC
3961 TTCATGATTA CAGCAATTAA TGTTTGCACA GAGCCCAGAT TATACAGCAG TGGGTCATTG
4021 TGCTTCATTA TTCAAGAATG AAGATAAAGA CAAATAGAGG ATTAGTAAAA TATATTAAAT
4081 GTGCAATACC ACTTAAATGA CTCTTAATGT TTATATTGAA TTTCCAAAGC GATTAAATAA
4141 AAAAGAGCTA TTTTTGTTA  TTGCCAAACA ATATTTTTTG TATTTCTCTA TTTTCATAAT
4201 GAGCAAATAG CATCCTATAA ATCTGTTTAT CTCTTCTTTG TAGTGTGTTT TCATATAAAT
4261 CCACAAGTAG AAAATCTTTT CATCTGTGGC ATATTTCTAT GACAAATGCA AGATCTAGAA
4321 AAATTAAATG TTTGATTATG CCATTTTGGA AATGCATATT TACCACCAAA CCTATGTGAC
4381 TGAATAATGT CAAATAAAAT TTTATGAATC ATTTTAAAAA AAAAAAAAAA AGGGCGGCCG
4441 C
```

FIG. 2B.

```
MAPVLSKDVADIESILALNPRTQSHAAALHSTLAKKLDKHWKRNPDKNCFHCEKLENNFGDIKHTTLGER        70
    S                   T   T C  S                    N        D

GALREAMRCLKCADAPCQKSCPTHLDIKSFITSISNKNYYGAAKMIFSDNPLGLTCGMVCPTSDLCVGGC       140
                           N            A

NLYATEEGSINIGGLQQFASEVFKAMNIPQIRNPCLPSQEKMPEAYSAKIALLGAGPASISCASFLARLG       210
                                   P   T  S   S PP  S          F

YSDITIFEKQEYVGGLSTSEIPQFRLPYDVVNFEIELMKDLGVKIICGKSLSENEITLNTLKEEGYKAAF       280
                                                  V  M S  K
                                                              NADPH/NADP
IGIGLPEPKTDDIFQFLTQDQGFYTSKDELPLIVAKSSKAGMCACHSPLPSIRGAVIVLGAGDTAFDCATS      350
      NK A                   G                        V

[A]LRCGARRVFLVFRKGFVNIRAVPEEVELAKEEKCEFLPFLSPRKVIVKGGRIVAVQFVRTEQDETGKWN      420
         I                M                                FAD
EDEDQIVHLKADVVISAFGSVLRDPKVKEALSPIKFNRWDLPEVDPETMQTSEPWVFAGGDIVGMANTTV      490
    M                   S                       G         A    V  L

ESVNDGKQASWYIHKYIQAQYGASVSAKPELPLFYTPVDLVDISVEMAGLKFINPFGLASAAPTTSSSMI      560
               V S                    I                          T A T

RRAFEAGWGFALTKTFSLDKDIVTNVSPRIVRGTTSGPMYGPGQSSFLNIELISEKTAAYWCQSVTELKA       630
                                       I       URACIL
DFPDNIVIASIMCSYNKNDWMELSRKAEASGADALELNLSCPHGMGERGMGLACGQDPELVRNICRWVRQ       700
                         T  AK S D

FIG. 3-1.
```

```
AVQIPFFAKLTPNVTDIVSIARAAKEGGADGVTATNTVSGLMGLKADGTPWPAVGAGKRTTYGGVSGTAI    770
                  N                      S D           IA

RPIALRAVTTIARALPGFPILATGGIDSAESGLQFLHSGASVLQVCSAVQNQDFTVIQDYCTGLKALLYL   840
    S                                                I        E

KSIEELQGWDGQSPGTESHQKGKPVPRIAELMGKKLPNFGPYLEQRKKIIAEEKMRLKEQNAAFPPLERK   910
       D   A V                      D S              N I    V S K S
                                                             [4Fe-4S]
PEIPKKPIPAIKDVIGKALQYLGTFGELSNIEQVVAVIDEEMCINCGKCYMTCNDSGYQAIQFDPETHLP   980
                             V              M
    [4Fe-4S]                              V   SS
TVTDTCTGCTICLSVCEIIDCIRMVSRTTPYEPKRGLPLAVNPVC.*                         1025
  I         V K

FIG. 3-2.
```

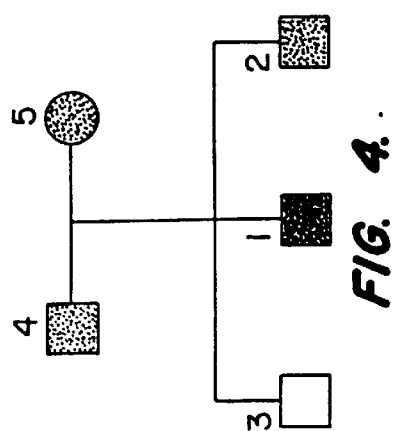
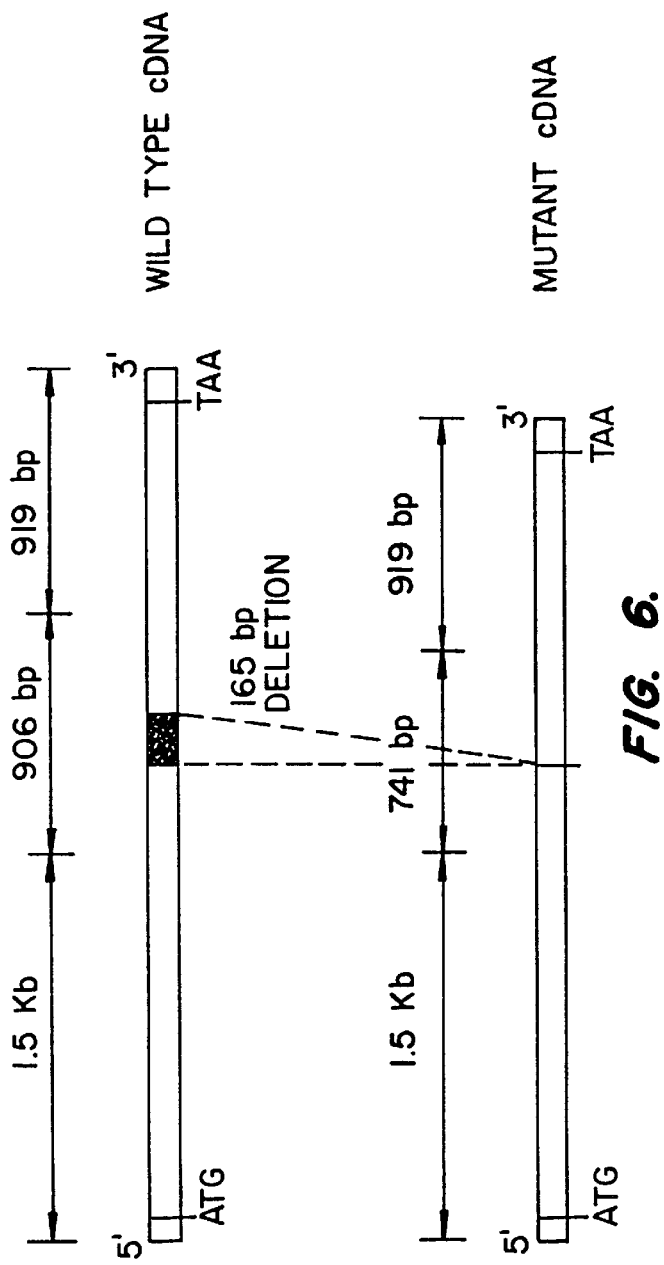
FIG. 4.
FIG. 6.

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 3957 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 88..3162

(ix) FEATURE:
        (A) NAME/KEY: misc_feature
        (B) LOCATION: 1..3957
        (D) OTHER INFORMATION: /product= "Human DPD"

(xi) SEQUENCE DESCRIPTION: SEQ ID NO:1:

```
AGACACGCTG TCACTTGGCT CTCTGGCTGG AGCTTGAGGA CGCAAGGAGG GTTTGTCACT        60

GGCAGACTCG AGACTGTAGG CACTGCC ATG GCC CCT GTG CTC AGT AAG GAC           111
                             Met Ala Pro Val Leu Ser Lys Asp
                               1               5

TCG GCG GAC ATC GAG AGT ATC CTG GCT TTA AAT CCT CGA ACA CAA ACT        159
Ser Ala Asp Ile Glu Ser Ile Leu Ala Leu Asn Pro Arg Thr Gln Thr
     10                  15                  20

CAT GCA ACT CTG TGT TCC ACT TCG GCC AAG AAA TTA GAC AAG AAA CAT        207
His Ala Thr Leu Cys Ser Thr Ser Ala Lys Lys Leu Asp Lys Lys His
 25                  30                  35                  40

TGG AAA AGA AAT CCT GAT AAG AAC TGC TTT AAT TGT GAG AAG CTG GAG        255
Trp Lys Arg Asn Pro Asp Lys Asn Cys Phe Asn Cys Glu Lys Leu Glu
                 45                  50                  55

AAT AAT TTT GAT GAC ATC AAG CAC ACG ACT CTT GGT GAG CGA GGA GCT        303
Asn Asn Phe Asp Asp Ile Lys His Thr Thr Leu Gly Glu Arg Gly Ala
             60                  65                  70

CTC CGA GAA GCA ATG AGA TGC CTG AAA TGT GCA GAT GCC CCG TGT CAG        351
Leu Arg Glu Ala Met Arg Cys Leu Lys Cys Ala Asp Ala Pro Cys Gln
         75                  80                  85

AAG AGC TGT CCA ACT AAT CTT GAT ATT AAA TCA TTC ATC ACA AGT ATT        399
Lys Ser Cys Pro Thr Asn Leu Asp Ile Lys Ser Phe Ile Thr Ser Ile
     90                  95                 100

GCA AAC AAG AAC TAT TAT GGA GCT GCT AAG ATG ATA TTT TCT GAC AAC        447
Ala Asn Lys Asn Tyr Tyr Gly Ala Ala Lys Met Ile Phe Ser Asp Asn
105                 110                 115                 120

CCA CTT GGT CTG ACT TGT GGA ATG GTA TGT CCA ACC TCT GAT CTA TGT        495
Pro Leu Gly Leu Thr Cys Gly Met Val Cys Pro Thr Ser Asp Leu Cys
                125                 130                 135

GTA GGT GGA TGC AAT TTA TAT GCC ACT GAA GAG GGA CCC ATT AAT ATT        543
Val Gly Gly Cys Asn Leu Tyr Ala Thr Glu Glu Gly Pro Ile Asn Ile
            140                 145                 150

GGT GGA TTG CAG CAA TTT GCT ACT GAG GTA TTC AAA GCA ATG AGT ATC        591
Gly Gly Leu Gln Gln Phe Ala Thr Glu Val Phe Lys Ala Met Ser Ile
        155                 160                 165

CCA CAG ATC AGA AAT CCT TCG CTG CCT CCC CCA GAA AAA ATG TCT GAA        639
Pro Gln Ile Arg Asn Pro Ser Leu Pro Pro Pro Glu Lys Met Ser Glu
170                 175                 180

GCC TAT TCT GCA AAG ATT GCT CTT TTT GGT GCT GGG CCT GCA AGT ATA        687
Ala Tyr Ser Ala Lys Ile Ala Leu Phe Gly Ala Gly Pro Ala Ser Ile
185                 190                 195                 200

AGT TGT GCT TCC TTT TTG GCT CGA TTG GGG TAC TCT GAC ATC ACT ATA        735
Ser Cys Ala Ser Phe Leu Ala Arg Leu Gly Tyr Ser Asp Ile Thr Ile
                205                 210                 215
```

| | | |
|---|---|---|
| TTT GAA AAA CAA GAA TAT GTT GGT GGT TTA AGT ACT TCT GAA ATT CCT<br>Phe Glu Lys Gln Glu Tyr Val Gly Gly Leu Ser Thr Ser Glu Ile Pro<br>220                     225                     230 | | 783 |
| CAG TTC CGG CTG CCG TAT GAT GTA GTG AAT TTT GAG ATT GAG CTA ATG<br>Gln Phe Arg Leu Pro Tyr Asp Val Val Asn Phe Glu Ile Glu Leu Met<br>     235                     240                     245 | | 831 |
| AAG GAC CTT GGT GTA AAG ATA ATT TGC GGT AAA AGC CTT TCA GTG AAT<br>Lys Asp Leu Gly Val Lys Ile Ile Cys Gly Lys Ser Leu Ser Val Asn<br>250                     255                     260 | | 879 |
| GAA ATG ACT CTT AGC ACT TTG AAA GAA AAA GGC TAC AAA GCT GCT TTC<br>Glu Met Thr Leu Ser Thr Leu Lys Glu Lys Gly Tyr Lys Ala Ala Phe<br>265                     270                     275                     280 | | 927 |
| ATT GGA ATA GGT TTG CCA GAA CCC AAT AAA GAT GCC ATC TTC CAA GGC<br>Ile Gly Ile Gly Leu Pro Glu Pro Asn Lys Asp Ala Ile Phe Gln Gly<br>                     285                     290                     295 | | 975 |
| CTG ACG CAG GAC CAG GGG TTT TAT ACA TCC AAA GAC TTT TTG CCA CTT<br>Leu Thr Gln Asp Gln Gly Phe Tyr Thr Ser Lys Asp Phe Leu Pro Leu<br>               300                     305                     310 | | 1023 |
| GTA GCC AAA GGC AGT AAA GCA GGA ATG TGC GCC TGT CAC TCT CCA TTG<br>Val Ala Lys Gly Ser Lys Ala Gly Met Cys Ala Cys His Ser Pro Leu<br>             315                     320                     325 | | 1071 |
| CCA TCG ATA CGG GGA GTC GTG ATT GTA CTT GGA GCT GGA GAC ACT GCC<br>Pro Ser Ile Arg Gly Val Val Ile Val Leu Gly Ala Gly Asp Thr Ala<br>330                     335                     340 | | 1119 |
| TTC GAC TGT GCA ACA TCT GCT CTA CGT TGT GGA GCT CGC CGA GTG TTC<br>Phe Asp Cys Ala Thr Ser Ala Leu Arg Cys Gly Ala Arg Arg Val Phe<br>345                     350                     355                     360 | | 1167 |
| ATC GTC TTC AGA AAA GGC TTT GTT AAT ATA AGA GCT GTC CCT GAG GAG<br>Ile Val Phe Arg Lys Gly Phe Val Asn Ile Arg Ala Val Pro Glu Glu<br>                     365                     370                     375 | | 1215 |
| ATG GAG CTT GCT AAG GAA GAA AAG TGT GAA TTT CTG CCA TTC CTG TCC<br>Met Glu Leu Ala Lys Glu Glu Lys Cys Glu Phe Leu Pro Phe Leu Ser<br>             380                     385                     390 | | 1263 |
| CCA CGG AAG GTT ATA GTA AAA GGT GGG AGA ATT GTT GCT ATG CAG TTT<br>Pro Arg Lys Val Ile Val Lys Gly Gly Arg Ile Val Ala Met Gln Phe<br>     395                     400                     405 | | 1311 |
| GTT CGG ACA GAG CAA GAT GAA ACT GGA AAA TGG AAT GAA GAT GAA GAT<br>Val Arg Thr Glu Gln Asp Glu Thr Gly Lys Trp Asn Glu Asp Glu Asp<br>410                     415                     420 | | 1359 |
| CAG ATG GTC CAT CTG AAA GCC GAT GTG GTC ATC AGT GCC TTT GGT TCA<br>Gln Met Val His Leu Lys Ala Asp Val Val Ile Ser Ala Phe Gly Ser<br>425                     430                     435                     440 | | 1407 |
| GTT CTG AGT GAT CCT AAA GTA AAA GAA GCC TTG AGC CCT ATA AAA TTT<br>Val Leu Ser Asp Pro Lys Val Lys Glu Ala Leu Ser Pro Ile Lys Phe<br>               445                     450                     455 | | 1455 |
| AAC AGA TGG GGT CTC CCA GAA GTA GAT CCA GAA ACT ATG CAA ACT AGT<br>Asn Arg Trp Gly Leu Pro Glu Val Asp Pro Glu Thr Met Gln Thr Ser<br>             460                     465                     470 | | 1503 |
| GAA GCA TGG GTA TTT GCA GGT GGT GAT GTC GTT GGT TTG GCT AAC ACT<br>Glu Ala Trp Val Phe Ala Gly Gly Asp Val Val Gly Leu Ala Asn Thr<br>             475                     480                     485 | | 1551 |
| ACA GTG GAA TCG GTG AAT GAT GGA AAG CAA GCT TCT TGG TAC ATT CAC<br>Thr Val Glu Ser Val Asn Asp Gly Lys Gln Ala Ser Trp Tyr Ile His<br>490                     495                     500 | | 1599 |
| AAA TAC GTA CAG TCA CAA TAT GGA GCT TCC GTT TCT GCC AAG CCT GAA<br>Lys Tyr Val Gln Ser Gln Tyr Gly Ala Ser Val Ser Ala Lys Pro Glu<br>505                     510                     515                     520 | | 1647 |
| CTA CCC CTC TTT TAC ACT CCT ATT GAT CTG GTG GAC ATT AGT GTA GAA<br>Leu Pro Leu Phe Tyr Thr Pro Ile Asp Leu Val Asp Ile Ser Val Glu<br>                     525                     530                     535 | | 1695 |

-continued

| | |
|---|---|
| ATG GCC GGA TTG AAG TTT ATA AAT CCT TTT GGT CTT GCT AGC GCA ACT<br>Met Ala Gly Leu Lys Phe Ile Asn Pro Phe Gly Leu Ala Ser Ala Thr<br>540          545          550 | 1743 |
| CCA GCC ACC AGC ACA TCA ATG ATT CGA AGA GCT TTT GAA GCT GGA TGG<br>Pro Ala Thr Ser Thr Ser Met Ile Arg Arg Ala Phe Glu Ala Gly Trp<br>555          560          565 | 1791 |
| GGT TTT GCC CTC ACC AAA ACT TTC TCT CTT GAT AAG GAC ATT GTG ACA<br>Gly Phe Ala Leu Thr Lys Thr Phe Ser Leu Asp Lys Asp Ile Val Thr<br>570          575          580 | 1839 |
| AAT GTT TCC CCC AGA ATC ATC CGG GGA ACC ACC TCT GGC CCC ATG TAT<br>Asn Val Ser Pro Arg Ile Ile Arg Gly Thr Thr Ser Gly Pro Met Tyr<br>585          590          595          600 | 1887 |
| GGC CCT GGA CAA AGC TCC TTT CTG AAT ATT GAG CTC ATC AGT GAG AAA<br>Gly Pro Gly Gln Ser Ser Phe Leu Asn Ile Glu Leu Ile Ser Glu Lys<br>605          610          615 | 1935 |
| ACG GCT GCA TAT TGG TGT CAA AGT GTC ACT GAA CTA AAG GCT GAC TTC<br>Thr Ala Ala Tyr Trp Cys Gln Ser Val Thr Glu Leu Lys Ala Asp Phe<br>620          625          630 | 1983 |
| CCA GAC AAC ATT GTG ATT GCT AGC ATT ATG TGC AGT TAC AAT AAA AAT<br>Pro Asp Asn Ile Val Ile Ala Ser Ile Met Cys Ser Tyr Asn Lys Asn<br>635          640          645 | 2031 |
| GAC TGG ACG GAA CTT GCC AAG AAG TCT GAG GAT TCT GGA GCA GAT GCC<br>Asp Trp Thr Glu Leu Ala Lys Lys Ser Glu Asp Ser Gly Ala Asp Ala<br>650          655          660 | 2079 |
| CTG GAG TTA AAT TTA TCA TGT CCA CAT GGC ATG GGA GAA AGA GGA ATG<br>Leu Glu Leu Asn Leu Ser Cys Pro His Gly Met Gly Glu Arg Gly Met<br>665          670          675          680 | 2127 |
| GGC CTG GCC TGT GGG CAG GAT CCA GAG CTG GTG CGG AAC ATC TGC CGC<br>Gly Leu Ala Cys Gly Gln Asp Pro Glu Leu Val Arg Asn Ile Cys Arg<br>685          690          695 | 2175 |
| TGG GTT AGG CAA GCT GTT CAG ATT CCT TTT TTT GCC AAG CTG ACC CCA<br>Trp Val Arg Gln Ala Val Gln Ile Pro Phe Phe Ala Lys Leu Thr Pro<br>700          705          710 | 2223 |
| AAT GTC ACT GAT ATT GTG AGC ATC GCA AGA GCT GCA AAG GAA GGT GGT<br>Asn Val Thr Asp Ile Val Ser Ile Ala Arg Ala Ala Lys Glu Gly Gly<br>715          720          725 | 2271 |
| GCC AAT GGC GTT ACA GCC ACC AAC ACT GTC TCA GGT CTG ATG GGA TTA<br>Ala Asn Gly Val Thr Ala Thr Asn Thr Val Ser Gly Leu Met Gly Leu<br>730          735          740 | 2319 |
| AAA TCT GAT GGC ACA CCT TGG CCA GCA GTG GGG ATT GCA AAG CGA ACT<br>Lys Ser Asp Gly Thr Pro Trp Pro Ala Val Gly Ile Ala Lys Arg Thr<br>745          750          755          760 | 2367 |
| ACA TAT GGA GGA GTG TCT GGG ACA GCA ATC AGA CCT ATT GCT TTG AGA<br>Thr Tyr Gly Gly Val Ser Gly Thr Ala Ile Arg Pro Ile Ala Leu Arg<br>765          770          775 | 2415 |
| GCT GTG ACC TCC ATT GCT CGT GCT CTG CCT GGA TTT CCC ATT TTG GCT<br>Ala Val Thr Ser Ile Ala Arg Ala Leu Pro Gly Phe Pro Ile Leu Ala<br>780          785          790 | 2463 |
| ACT GGT GGA ATT GAC TCT GCT GAA AGT GGT CTT CAG TTT CTC CAT AGT<br>Thr Gly Gly Ile Asp Ser Ala Glu Ser Gly Leu Gln Phe Leu His Ser<br>795          800          805 | 2511 |
| GGT GCT TCC GTC CTC CAG GTA TGC AGT GCC ATT CAG AAT CAG GAT TTC<br>Gly Ala Ser Val Leu Gln Val Cys Ser Ala Ile Gln Asn Gln Asp Phe<br>810          815          820 | 2559 |
| ACT GTG ATC GAA GAC TAC TGC ACT GGC CTC AAA GCC CTG CTT TAT CTG<br>Thr Val Ile Glu Asp Tyr Cys Thr Gly Leu Lys Ala Leu Leu Tyr Leu<br>825          830          835          840 | 2607 |
| AAA AGC ATT GAA GAA CTA CAA GAC TGG GAT GGA CAG AGT CCA GCT ACT<br>Lys Ser Ile Glu Glu Leu Gln Asp Trp Asp Gly Gln Ser Pro Ala Thr<br>845          850          855 | 2655 |

```
GTG AGT CAC CAG AAA GGG AAA CCA GTT CCA CGT ATA GCT GAA CTC ATG      2703
Val Ser His Gln Lys Gly Lys Pro Val Pro Arg Ile Ala Glu Leu Met
        860                 865                 870

GAC AAG AAA CTG CCA AGT TTT GGA CCT TAT CTG GAA CAG CGC AAG AAA      2751
Asp Lys Lys Leu Pro Ser Phe Gly Pro Tyr Leu Glu Gln Arg Lys Lys
    875                 880                 885

ATC ATA GCA GAA AAC AAG ATT AGA CTG AAA GAA CAA AAT GTA GCT TTT      2799
Ile Ile Ala Glu Asn Lys Ile Arg Leu Lys Glu Gln Asn Val Ala Phe
890                 895                 900

TCA CCA CTT AAG AGA AGC TGT TTT ATC CCC AAA AGG CCT ATT CCT ACC      2847
Ser Pro Leu Lys Arg Ser Cys Phe Ile Pro Lys Arg Pro Ile Pro Thr
905                 910                 915                 920

ATC AAG GAT GTA ATA GGA AAA GCA CTG CAG TAC CTT GGA ACA TTT GGT      2895
Ile Lys Asp Val Ile Gly Lys Ala Leu Gln Tyr Leu Gly Thr Phe Gly
            925                 930                 935

GAA TTG AGC AAC GTA GAG CAA GTT GTG GCT ATG ATT GAT GAA GAA ATG      2943
Glu Leu Ser Asn Val Glu Gln Val Val Ala Met Ile Asp Glu Glu Met
        940                 945                 950

TGT ATC AAC TGT GGT AAA TGC TAC ATG ACC TGT AAT GAT TCT GGC TAC      2991
Cys Ile Asn Cys Gly Lys Cys Tyr Met Thr Cys Asn Asp Ser Gly Tyr
    955                 960                 965

CAG GCT ATA CAG TTT GAT CCA GAA ACC CAC CTG CCC ACC ATA ACC GAC      3039
Gln Ala Ile Gln Phe Asp Pro Glu Thr His Leu Pro Thr Ile Thr Asp
970                 975                 980

ACT TGT ACA GGC TGT ACT CTG TGT CTC AGT GTT TGC CCT ATT GTC GAC      3087
Thr Cys Thr Gly Cys Thr Leu Cys Leu Ser Val Cys Pro Ile Val Asp
985                 990                 995                 1000

TGC ATC AAA ATG GTT TCC AGG ACA ACA CCT TAT GAA CCA AAG AGA GGC      3135
Cys Ile Lys Met Val Ser Arg Thr Thr Pro Tyr Glu Pro Lys Arg Gly
            1005                1010                1015

GTA CCC TTA TCT GTG AAT CCG GTG TGT TAAGGTGATT TGTGAAACAG            3182
Val Pro Leu Ser Val Asn Pro Val Cys
                1020                1025

TTGCTGTGAA CTTTCATGTC ACCTACATAT GCTGATCTCT TAAAATCATG ATCCTTGTGT    3242

TCAGCTCTTT CCAAATTAAA ACAAATATAC ATTTTCTAAA TAAAAATATG TAATTTCAAA    3302

ATACATTTGT AAGTGTAAAA AATGTCTCAT GTCAATGACC ATTCAATTAG TGGCATAAAA    3362

TAGAATAATT CTTTTCTGAG GATAGTAGTT AAATAACTGT GTGGCAGTTA ATTGGATGTT    3422

CACTGCCAGT TGTCTTATGT GAAAAATTAA CTTTTTGTGT GGCAATTAGT GTGACAGTTT    3482

CCAAATTGCC CTATGCTGTG CTCCATATTT GATTTCTAAT TGTAAGTGAA ATTAAGCATT    3542

TTGAAACAAA GTACTCTTTA ACATACAAGA AAATGTATCC AAGGAAACAT TTTATCAATA    3602

AAAATTACCT TTAATTTTAA TGCTGTTTCT AAGAAAATGT AGTTAGCTCC ATAAAGTACA    3662

AATGAAGAAA GTCAAAAATT ATTTGCTATG GCAGGATAAG AAAGCCTAAA ATTGAGTTTG    3722

TGGACTTTAT TAAGTAAAAT CCCCTTCGCT GAAATTGCTT ATTTTTGGTG TTGGATAGAG    3782

GATAGGGAGA ATATTTACTA ACTAAATACC ATTCACTACT CATGCGTGAG ATGGGTGTAC    3842

AAACTCATCC TCTTTTAATG GCATTTCTCT TTAAACTATG TTCCTAACCA AATGAGATGA    3902

TAGGATAGAT CCTGGTTACC ACTCTTTTAC TGTGCACATA TGGGCCCCGG AATTC         3957
```

(2) INFORMATION FOR SEQ ID NO:2:

(i) SEQUENCE CHARACTERISTICS:
        (A) LENGTH: 1025 amino acids
        (B) TYPE: amino acid
        (D) TOPOLOGY: linear (ii) MOLECULE TYPE: protein -continued (xi) SEQUENCE DESCRIPTION: SEQ ID NO:2:

```
Met Ala Pro Val Leu Ser Lys Asp Ser Ala Asp Ile Glu Ser Ile Leu
 1               5                  10                  15

Ala Leu Asn Pro Arg Thr Gln Thr His Ala Thr Leu Cys Ser Thr Ser
            20                  25                  30

Ala Lys Lys Leu Asp Lys Lys His Trp Lys Arg Asn Pro Asp Lys Asn
        35                  40                  45

Cys Phe Asn Cys Glu Lys Leu Glu Asn Asn Phe Asp Asp Ile Lys His
    50                  55                  60

Thr Thr Leu Gly Glu Arg Gly Ala Leu Arg Glu Ala Met Arg Cys Leu
65                  70                  75                  80

Lys Cys Ala Asp Ala Pro Cys Gln Lys Ser Cys Pro Thr Asn Leu Asp
                85                  90                  95

Ile Lys Ser Phe Ile Thr Ser Ile Ala Asn Lys Asn Tyr Tyr Gly Ala
            100                 105                 110

Ala Lys Met Ile Phe Ser Asp Asn Pro Leu Gly Leu Thr Cys Gly Met
        115                 120                 125

Val Cys Pro Thr Ser Asp Leu Cys Val Gly Gly Cys Asn Leu Tyr Ala
130                 135                 140

Thr Glu Glu Gly Pro Ile Asn Ile Gly Gly Leu Gln Gln Phe Ala Thr
145                 150                 155                 160

Glu Val Phe Lys Ala Met Ser Ile Pro Gln Ile Arg Asn Pro Ser Leu
                165                 170                 175

Pro Pro Pro Glu Lys Met Ser Glu Ala Tyr Ser Ala Lys Ile Ala Leu
            180                 185                 190

Phe Gly Ala Gly Pro Ala Ser Ile Ser Cys Ala Ser Phe Leu Ala Arg
        195                 200                 205

Leu Gly Tyr Ser Asp Ile Thr Ile Phe Glu Lys Gln Glu Tyr Val Gly
    210                 215                 220

Gly Leu Ser Thr Ser Glu Ile Pro Gln Phe Arg Leu Pro Tyr Asp Val
225                 230                 235                 240

Val Asn Phe Glu Ile Glu Leu Met Lys Asp Leu Gly Val Lys Ile Ile
                245                 250                 255

Cys Gly Lys Ser Leu Ser Val Asn Glu Met Thr Leu Ser Thr Leu Lys
            260                 265                 270

Glu Lys Gly Tyr Lys Ala Ala Phe Ile Gly Ile Gly Leu Pro Glu Pro
        275                 280                 285

Asn Lys Asp Ala Ile Phe Gln Gly Leu Thr Gln Asp Gln Gly Phe Tyr
    290                 295                 300

Thr Ser Lys Asp Phe Leu Pro Leu Val Ala Lys Gly Ser Lys Ala Gly
305                 310                 315                 320

Met Cys Ala Cys His Ser Pro Leu Pro Ser Ile Arg Gly Val Val Ile
                325                 330                 335

Val Leu Gly Ala Gly Asp Thr Ala Phe Asp Cys Ala Thr Ser Ala Leu
            340                 345                 350

Arg Cys Gly Ala Arg Arg Val Phe Ile Val Phe Arg Lys Gly Phe Val
        355                 360                 365

Asn Ile Arg Ala Val Pro Glu Glu Met Glu Leu Ala Lys Glu Glu Lys
    370                 375                 380

Cys Glu Phe Leu Pro Phe Leu Ser Pro Arg Lys Val Ile Val Lys Gly
385                 390                 395                 400

Gly Arg Ile Val Ala Met Gln Phe Val Arg Thr Glu Gln Asp Glu Thr
                405                 410                 415
```

-continued

```
Gly Lys Trp Asn Glu Asp Glu Asp Gln Met Val His Leu Lys Ala Asp
            420                 425                 430

Val Val Ile Ser Ala Phe Gly Ser Val Leu Ser Asp Pro Lys Val Lys
            435                 440                 445

Glu Ala Leu Ser Pro Ile Lys Phe Asn Arg Trp Gly Leu Pro Glu Val
450                 455                 460

Asp Pro Glu Thr Met Gln Thr Ser Glu Ala Trp Val Phe Ala Gly Gly
465                 470                 475                 480

Asp Val Val Gly Leu Ala Asn Thr Thr Val Glu Ser Val Asn Asp Gly
                485                 490                 495

Lys Gln Ala Ser Trp Tyr Ile His Lys Tyr Val Gln Ser Gln Tyr Gly
                500                 505                 510

Ala Ser Val Ser Ala Lys Pro Glu Leu Pro Leu Phe Tyr Thr Pro Ile
            515                 520                 525

Asp Leu Val Asp Ile Ser Val Glu Met Ala Gly Leu Lys Phe Ile Asn
530                 535                 540

Pro Phe Gly Leu Ala Ser Ala Thr Pro Ala Thr Ser Thr Ser Met Ile
545                 550                 555                 560

Arg Arg Ala Phe Glu Ala Gly Trp Gly Phe Ala Leu Thr Lys Thr Phe
                565                 570                 575

Ser Leu Asp Lys Asp Ile Val Thr Asn Val Ser Pro Arg Ile Ile Arg
            580                 585                 590

Gly Thr Thr Ser Gly Pro Met Tyr Gly Pro Gly Gln Ser Ser Phe Leu
            595                 600                 605

Asn Ile Glu Leu Ile Ser Glu Lys Thr Ala Ala Tyr Trp Cys Gln Ser
            610                 615                 620

Val Thr Glu Leu Lys Ala Asp Phe Pro Asp Asn Ile Val Ile Ala Ser
625                 630                 635                 640

Ile Met Cys Ser Tyr Asn Lys Asn Asp Trp Thr Glu Leu Ala Lys Lys
                645                 650                 655

Ser Glu Asp Ser Gly Ala Asp Ala Leu Glu Leu Asn Leu Ser Cys Pro
                660                 665                 670

His Gly Met Gly Glu Arg Gly Met Gly Leu Ala Cys Gly Gln Asp Pro
            675                 680                 685

Glu Leu Val Arg Asn Ile Cys Arg Trp Val Arg Gln Ala Val Gln Ile
690                 695                 700

Pro Phe Phe Ala Lys Leu Thr Pro Asn Val Thr Asp Ile Val Ser Ile
705                 710                 715                 720

Ala Arg Ala Ala Lys Glu Gly Gly Ala Asn Gly Val Thr Ala Thr Asn
                725                 730                 735

Thr Val Ser Gly Leu Met Gly Leu Lys Ser Asp Gly Thr Pro Trp Pro
            740                 745                 750

Ala Val Gly Ile Ala Lys Arg Thr Thr Tyr Gly Gly Val Ser Gly Thr
            755                 760                 765

Ala Ile Arg Pro Ile Ala Leu Arg Ala Val Thr Ser Ile Ala Arg Ala
770                 775                 780

Leu Pro Gly Phe Pro Ile Leu Ala Thr Gly Gly Ile Asp Ser Ala Glu
785                 790                 795                 800

Ser Gly Leu Gln Phe Leu His Ser Gly Ala Ser Val Leu Gln Val Cys
                805                 810                 815

Ser Ala Ile Gln Asn Gln Asp Phe Thr Val Ile Glu Asp Tyr Cys Thr
            820                 825                 830

Gly Leu Lys Ala Leu Leu Tyr Leu Lys Ser Ile Glu Glu Leu Gln Asp
            835                 840                 845
```

```
Trp Asp Gly Gln Ser Pro Ala Thr Val Ser His Gln Lys Gly Lys Pro
850                 855                 860

Val Pro Arg Ile Ala Glu Leu Met Asp Lys Lys Leu Pro Ser Phe Gly
865                 870                 875                 880

Pro Tyr Leu Glu Gln Arg Lys Lys Ile Ile Ala Glu Asn Lys Ile Arg
                885                 890                 895

Leu Lys Glu Gln Asn Val Ala Phe Ser Pro Leu Lys Arg Ser Cys Phe
                900                 905                 910

Ile Pro Lys Arg Pro Ile Pro Thr Ile Lys Asp Val Ile Gly Lys Ala
            915                 920                 925

Leu Gln Tyr Leu Gly Thr Phe Gly Glu Leu Ser Asn Val Glu Gln Val
        930                 935                 940

Val Ala Met Ile Asp Glu Met Cys Ile Asn Cys Gly Lys Cys Tyr
945                 950                 955                 960

Met Thr Cys Asn Asp Ser Gly Tyr Gln Ala Ile Gln Phe Asp Pro Glu
                965                 970                 975

Thr His Leu Pro Thr Ile Thr Asp Thr Cys Thr Gly Cys Thr Leu Cys
                980                 985                 990

Leu Ser Val Cys Pro Ile Val Asp Cys Ile Lys Met Val Ser Arg Thr
            995                 1000                1005

Thr Pro Tyr Glu Pro Lys Arg Gly Val Pro Leu Ser Val Asn Pro Val
    1010                1015                1020

Cys
1025

(2) INFORMATION FOR SEQ ID NO:3:

(i) SEQUENCE CHARACTERISTICS:
        (A) LENGTH: 4447 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 88..3162

(ix) FEATURE:
        (A) NAME/KEY: misc_feature
        (B) LOCATION: 1..4447
        (D) OTHER INFORMATION: /product= "Pig DPD"

(xi) SEQUENCE DESCRIPTION: SEQ ID NO:3:

GGACACTCGA CCCACGCGTC CGCCGGCCGG AGGCGGAGGA CGCGGGGAGG GCCCGCCGGT        60

GGGAGACTCC AAGCTGTCGG CATCGCC ATG GCC CCT GTG CTG AGC AAG GAC          111
                              Met Ala Pro Val Leu Ser Lys Asp
                               1               5

GTG GCG GAC ATC GAG AGT ATC CTG GCT TTA AAT CCT CGA ACA CAG TCT        159
Val Ala Asp Ile Glu Ser Ile Leu Ala Leu Asn Pro Arg Thr Gln Ser
    10                  15                  20

CAT GCA GCC CTT CAT TCC ACT TTG GCC AAG AAA TTG GAT AAG AAA CAC        207
His Ala Ala Leu His Ser Thr Leu Ala Lys Lys Leu Asp Lys Lys His
 25                  30                  35                  40

TGG AAA AGA AAT CCC GAT AAG AAC TGC TTT CAT TGC GAG AAG CTG GAG        255
Trp Lys Arg Asn Pro Asp Lys Asn Cys Phe His Cys Glu Lys Leu Glu
                 45                  50                  55

AAT AAT TTT GGT GAC ATC AAG CAC ACG ACT CTT GGT GAG CGA GGA GCT        303
Asn Asn Phe Gly Asp Ile Lys His Thr Thr Leu Gly Glu Arg Gly Ala
             60                  65                  70
```

```
CTC CGA GAA GCA ATG AGA TGC CTG AAA TGT GCC GAT GCT CCC TGT CAG            351
Leu Arg Glu Ala Met Arg Cys Leu Lys Cys Ala Asp Ala Pro Cys Gln
        75                  80                  85

AAG AGC TGT CCA ACT CAT CTA GAT ATC AAA TCA TTC ATC ACA AGT ATC            399
Lys Ser Cys Pro Thr His Leu Asp Ile Lys Ser Phe Ile Thr Ser Ile
    90                  95                  100

TCA AAT AAG AAC TAT TAT GGA GCT GCT AAG ATG ATT TTT TCT GAC AAC            447
Ser Asn Lys Asn Tyr Tyr Gly Ala Ala Lys Met Ile Phe Ser Asp Asn
105                 110                 115                 120

CCT CTT GGT CTG ACC TGT GGA ATG GTA TGT CCA ACC TCT GAT CTT TGT            495
Pro Leu Gly Leu Thr Cys Gly Met Val Cys Pro Thr Ser Asp Leu Cys
            125                 130                 135

GTA GGA GGA TGC AAT TTA TAT GCA ACT GAA GAG GGA TCA ATT AAT ATT            543
Val Gly Gly Cys Asn Leu Tyr Ala Thr Glu Glu Gly Ser Ile Asn Ile
        140                 145                 150

GGT GGA TTG CAG CAG TTT GCT TCT GAG GTG TTC AAA GCA ATG AAT ATC            591
Gly Gly Leu Gln Gln Phe Ala Ser Glu Val Phe Lys Ala Met Asn Ile
    155                 160                 165

CCA CAA ATC AGG AAT CCT TGT CTG CCA TCC CAA GAG AAA ATG CCT GAA            639
Pro Gln Ile Arg Asn Pro Cys Leu Pro Ser Gln Glu Lys Met Pro Glu
170                 175                 180

GCT TAT TCT GCA AAG ATT GCT CTT TTG GGT GCT GGG CCT GCA AGT ATA            687
Ala Tyr Ser Ala Lys Ile Ala Leu Leu Gly Ala Gly Pro Ala Ser Ile
185                 190                 195                 200

AGC TGT GCT TCC TTC TTG GCT CGA TTA GGC TAC TCT GAC ATC ACT ATA            735
Ser Cys Ala Ser Phe Leu Ala Arg Leu Gly Tyr Ser Asp Ile Thr Ile
            205                 210                 215

TTT GAA AAA CAA GAA TAT GTT GGT GGT TTA AGT ACT TCT GAA ATC CCT            783
Phe Glu Lys Gln Glu Tyr Val Gly Gly Leu Ser Thr Ser Glu Ile Pro
        220                 225                 230

CAG TTC CGG CTG CCA TAT GAT GTA GTG AAT TTT GAG ATT GAG CTT ATG            831
Gln Phe Arg Leu Pro Tyr Asp Val Val Asn Phe Glu Ile Glu Leu Met
    235                 240                 245

AAG GAC CTT GGT GTA AAG ATA ATT TGT GGT AAA AGC CTT TCA GAG AAT            879
Lys Asp Leu Gly Val Lys Ile Ile Cys Gly Lys Ser Leu Ser Glu Asn
250                 255                 260

GAA ATT ACT CTC AAC ACT TTA AAA GAA GAA GGG TAT AAA GCT GCT TTC            927
Glu Ile Thr Leu Asn Thr Leu Lys Glu Glu Gly Tyr Lys Ala Ala Phe
265                 270                 275                 280

ATT GGT ATA GGT TTG CCA GAA CCC AAA ACG GAT GAC ATC TTC CAA GGC            975
Ile Gly Ile Gly Leu Pro Glu Pro Lys Thr Asp Asp Ile Phe Gln Gly
            285                 290                 295

CTG ACA CAG GAC CAG GGG TTT TAC ACA TCC AAA GAC TTT CTG CCC CTT           1023
Leu Thr Gln Asp Gln Gly Phe Tyr Thr Ser Lys Asp Phe Leu Pro Leu
        300                 305                 310

GTA GCC AAA AGC AGT AAA GCA GGA ATG TGT GCC TGT CAC TCT CCA TTG           1071
Val Ala Lys Ser Ser Lys Ala Gly Met Cys Ala Cys His Ser Pro Leu
    315                 320                 325

CCA TCG ATA CGG GGA GCC GTG ATT GTA CTC GGA GCT GGA GAC ACA GCT           1119
Pro Ser Ile Arg Gly Ala Val Ile Val Leu Gly Ala Gly Asp Thr Ala
330                 335                 340

TTC GAC TGT GCA ACA TCC GCT TTA CGT TGT GGA GCC CGC CGA GTG TTC           1167
Phe Asp Cys Ala Thr Ser Ala Leu Arg Cys Gly Ala Arg Arg Val Phe
345                 350                 355                 360

CTC GTC TTC AGA AAA GGC TTT GTT AAT ATA AGA GCT GTC CCT GAG GAG           1215
Leu Val Phe Arg Lys Gly Phe Val Asn Ile Arg Ala Val Pro Glu Glu
            365                 370                 375

GTG GAG CTT GCT AAG GAA GAA AAA TGT GAA TTT TTG CCT TTC CTG TCC           1263
Val Glu Leu Ala Lys Glu Glu Lys Cys Glu Phe Leu Pro Phe Leu Ser
        380                 385                 390
```

```
CCA CGG AAG GTT ATA GTT AAA GGT GGG AGA ATT GTT GCC GTG CAA TTT         1311
Pro Arg Lys Val Ile Val Lys Gly Gly Arg Ile Val Ala Val Gln Phe
        395                 400                 405

GTT CGA ACA GAA CAA GAT GAA ACT GGA AAA TGG AAT GAA GAT GAA GAT         1359
Val Arg Thr Glu Gln Asp Glu Thr Gly Lys Trp Asn Glu Asp Glu Asp
410                 415                 420

CAG ATA GTC CAT CTG AAG GCT GAT GTG GTC ATC AGT GCC TTT GGC TCA         1407
Gln Ile Val His Leu Lys Ala Asp Val Val Ile Ser Ala Phe Gly Ser
425                 430                 435                 440

GTG CTG AGG GAT CCT AAA GTA AAA GAA GCC TTG AGC CCT ATA AAA TTT         1455
Val Leu Arg Asp Pro Lys Val Lys Glu Ala Leu Ser Pro Ile Lys Phe
                445                 450                 455

AAC AGA TGG GAT CTC CCA GAA GTA GAT CCA GAA ACT ATG CAA ACC AGT         1503
Asn Arg Trp Asp Leu Pro Glu Val Asp Pro Glu Thr Met Gln Thr Ser
        460                 465                 470

GAA CCA TGG GTG TTT GCA GGT GGT GAT ATC GTT GGT ATG GCT AAC ACT         1551
Glu Pro Trp Val Phe Ala Gly Gly Asp Ile Val Gly Met Ala Asn Thr
        475                 480                 485

ACG GTG GAA TCC GTA AAT GAC GGA AAG CAG GCC TCC TGG TAC ATT CAC         1599
Thr Val Glu Ser Val Asn Asp Gly Lys Gln Ala Ser Trp Tyr Ile His
490                 495                 500

AAA TAT ATC CAG GCC CAA TAT GGA GCT TCA GTT TCT GCC AAG CCC GAA         1647
Lys Tyr Ile Gln Ala Gln Tyr Gly Ala Ser Val Ser Ala Lys Pro Glu
505                 510                 515                 520

CTG CCC CTG TTT TAT ACG CCT GTT GAC CTG GTG GAC ATC AGC GTG GAA         1695
Leu Pro Leu Phe Tyr Thr Pro Val Asp Leu Val Asp Ile Ser Val Glu
                525                 530                 535

ATG GCT GGA TTA AAG TTT ATA AAT CCT TTT GGT CTT GCC AGT GCA GCT         1743
Met Ala Gly Leu Lys Phe Ile Asn Pro Phe Gly Leu Ala Ser Ala Ala
        540                 545                 550

CCA ACT ACC AGT TCA TCG ATG ATT CGA AGA GCT TTT GAA GCT GGA TGG         1791
Pro Thr Thr Ser Ser Ser Met Ile Arg Arg Ala Phe Glu Ala Gly Trp
        555                 560                 565

GGT TTT GCC CTG ACC AAA ACT TTC TCT CTT GAT AAG GAC ATA GTG ACA         1839
Gly Phe Ala Leu Thr Lys Thr Phe Ser Leu Asp Lys Asp Ile Val Thr
570                 575                 580

AAT GTC TCA CCC AGA ATC GTC CGG GGG ACT ACC TCT GGC CCC ATG TAC         1887
Asn Val Ser Pro Arg Ile Val Arg Gly Thr Thr Ser Gly Pro Met Tyr
585                 590                 595                 600

GGC CCT GGA CAA AGC TCC TTC CTG AAT ATT GAG CTC ATC AGT GAA AAA         1935
Gly Pro Gly Gln Ser Ser Phe Leu Asn Ile Glu Leu Ile Ser Glu Lys
                605                 610                 615

ACA GCT GCA TAT TGG TGT CAA AGT GTC ACT GAA CTA AAA GCT GAC TTT         1983
Thr Ala Ala Tyr Trp Cys Gln Ser Val Thr Glu Leu Lys Ala Asp Phe
        620                 625                 630

CCA GAC AAT ATT GTG ATC GCC AGC ATC ATG TGT AGT TAC AAC AAA AAT         2031
Pro Asp Asn Ile Val Ile Ala Ser Ile Met Cys Ser Tyr Asn Lys Asn
        635                 640                 645

GAC TGG ATG GAA CTC TCC AGA AAG GCT GAG GCC TCT GGA GCA GAT GCC         2079
Asp Trp Met Glu Leu Ser Arg Lys Ala Glu Ala Ser Gly Ala Asp Ala
650                 655                 660

TTG GAG TTA AAT CTG TCA TGT CCA CAC GGC ATG GGA GAA AGA GGA ATG         2127
Leu Glu Leu Asn Leu Ser Cys Pro His Gly Met Gly Glu Arg Gly Met
665                 670                 675                 680

GGC CTG GCT TGT GGG CAG GAT CCA GAG CTG GTG CGG AAC ATC TGT CGC         2175
Gly Leu Ala Cys Gly Gln Asp Pro Glu Leu Val Arg Asn Ile Cys Arg
                685                 690                 695

TGG GTT AGG CAA GCT GTT CAG ATT CCC TTT TTT GCC AAG TTG ACC CCA         2223
Trp Val Arg Gln Ala Val Gln Ile Pro Phe Phe Ala Lys Leu Thr Pro
        700                 705                 710
```

```
                                                    -continued

AAC GTC ACT GAT ATA GTA AGC ATC GCC AGA GCG GCC AAG GAA GGT GGC     2271
Asn Val Thr Asp Ile Val Ser Ile Ala Arg Ala Ala Lys Glu Gly Gly
            715                 720                 725

GCA GAT GGT GTT ACA GCC ACC AAC ACG GTC TCA GGT CTC ATG GGA TTA     2319
Ala Asp Gly Val Thr Ala Thr Asn Thr Val Ser Gly Leu Met Gly Leu
730                 735                 740

AAA GCC GAT GGC ACG CCC TGG CCA GCG GTG GGT GCT GGC AAG CGG ACT     2367
Lys Ala Asp Gly Thr Pro Trp Pro Ala Val Gly Ala Gly Lys Arg Thr
745                 750                 755                 760

ACA TAC GGA GGA GTG TCT GGC ACG GCC ATC AGA CCA ATT GCT TTG AGA     2415
Thr Tyr Gly Gly Val Ser Gly Thr Ala Ile Arg Pro Ile Ala Leu Arg
            765                 770                 775

GCT GTG ACC ACC ATT GCT CGT GCT TTG CCT GGA TTT CCC ATT TTG GCT     2463
Ala Val Thr Thr Ile Ala Arg Ala Leu Pro Gly Phe Pro Ile Leu Ala
            780                 785                 790

ACT GGT GGA ATT GAC TCA GCT GAA AGT GGA CTT CAG TTT CTC CAC AGT     2511
Thr Gly Gly Ile Asp Ser Ala Glu Ser Gly Leu Gln Phe Leu His Ser
            795                 800                 805

GGT GCT TCG GTC CTC CAG GTA TGC AGT GCT GTT CAG AAT CAG GAT TTC     2559
Gly Ala Ser Val Leu Gln Val Cys Ser Ala Val Gln Asn Gln Asp Phe
810                 815                 820

ACT GTC ATC CAA GAC TAT TGC ACT GGC CTC AAA GCC TTG CTT TAT CTG     2607
Thr Val Ile Gln Asp Tyr Cys Thr Gly Leu Lys Ala Leu Leu Tyr Leu
825                 830                 835                 840

AAA AGC ATT GAA GAA CTA CAA GGC TGG GAT GGG CAG AGT CCA GGT ACC     2655
Lys Ser Ile Glu Glu Leu Gln Gly Trp Asp Gly Gln Ser Pro Gly Thr
            845                 850                 855

GAG AGT CAC CAG AAG GGG AAA CCA GTT CCT CGT ATT GCT GAA CTC ATG     2703
Glu Ser His Gln Lys Gly Lys Pro Val Pro Arg Ile Ala Glu Leu Met
            860                 865                 870

GGA AAG AAA CTG CCA AAT TTT GGA CCT TAT CTG GAG CAA CGC AAG AAA     2751
Gly Lys Lys Leu Pro Asn Phe Gly Pro Tyr Leu Glu Gln Arg Lys Lys
            875                 880                 885

ATC ATA GCA GAG GAA AAG ATG AGA CTG AAA GAA CAA AAT GCA GCT TTT     2799
Ile Ile Ala Glu Glu Lys Met Arg Leu Lys Glu Gln Asn Ala Ala Phe
890                 895                 900

CCA CCA CTT GAG AGA AAA CCT TTT ATT CCC AAA AAG CCT ATT CCT GCT     2847
Pro Pro Leu Glu Arg Lys Pro Phe Ile Pro Lys Lys Pro Ile Pro Ala
905                 910                 915                 920

ATT AAG GAT GTA ATT GGA AAA GCA CTG CAG TAC CTT GGA ACG TTT GGT     2895
Ile Lys Asp Val Ile Gly Lys Ala Leu Gln Tyr Leu Gly Thr Phe Gly
            925                 930                 935

GAA CTG AGC AAC ATA GAG CAA GTT GTG GCT GTG ATC GAT GAA GAA ATG     2943
Glu Leu Ser Asn Ile Glu Gln Val Val Ala Val Ile Asp Glu Glu Met
            940                 945                 950

TGT ATC AAC TGT GGC AAA TGT TAC ATG ACC TGT AAT GAC TCT GGC TAC     2991
Cys Ile Asn Cys Gly Lys Cys Tyr Met Thr Cys Asn Asp Ser Gly Tyr
            955                 960                 965

CAG GCT ATC CAG TTT GAT CCC GAA ACC CAC CTG CCC ACC GTT ACT GAC     3039
Gln Ala Ile Gln Phe Asp Pro Glu Thr His Leu Pro Thr Val Thr Asp
970                 975                 980

ACT TGC ACA GGC TGT ACC CTG TGT CTC TCC GTC TGC CCT ATT ATC GAC     3087
Thr Cys Thr Gly Cys Thr Leu Cys Leu Ser Val Cys Pro Ile Ile Asp
985                 990                 995                 1000

TGC ATC AGA ATG GTT TCC AGG ACA ACA CCT TAC GAA CCA AAG AGA GGC     3135
Cys Ile Arg Met Val Ser Arg Thr Thr Pro Tyr Glu Pro Lys Arg Gly
            1005                1010                1015

TTG CCC TTG GCT GTG AAT CCG GTG TGC TGAGGTGATT CGTGGAACAG          3182
Leu Pro Leu Ala Val Asn Pro Val Cys
            1020                1025
```

```
TTGCTGTGAA CTTTGAGGTC ACCCCCATAT GCTGTCTTTT TAATTGTGGT TATTATACTC    3242

AGCTCTTTCT CAATGAAAAC AAATATAATA TTTCTAGATA AAAGTTCTAA ATACATGTCT    3302

AAATTTTAAA AACATCTAC TGCCAGAGCC CGTTCAATTA ATGGTCATAA AATAGAATCC     3362

TGCTTTTCTG AGGCTAGTTG TTCAATAACT GCTGCAGTTA ATTGGATGTT CTCCATCAGT    3422

TATCCATTAT GAAAAATATT AACTTTTTTG GTGGCAATTT CCAAATTGCC CTATGCTGTG    3482

CTCTGTCTTT GATTTCTAAT TGTAAGTGAA GTTAAGCATT TTAGAACAAA GTATAATTTA    3542

ACTTTCAAGC AAATGTTTCC AAGGAAACAT TTTATAATTA AAAATTACAA TTTAATTTTA    3602

ACACTGTTCC TAAGCAAATG TAATTAGCTC CATAAAGCTC AAATGAAGTC AAATAATTAT    3662

TTACTGTGGC AGGAAAAGAA AGCCAATGAG GGTTTGCAAA ACTTCTCTAA GGCCCTTTGG    3722

CTGAAATAAC TTCTCTTTGG TGCTACATAC TGAAAGTGAC TGTTTAATCA TCATTCATGT    3782

CACACCGTGC TCCCTCGCCC TCAGGCCTGA GATGGGTCTC CAGACTCCAC CAGTGAATCA    3842

GCATGACACC TTCTTTAACT GTGTGAGCGA CGTTCCTAAC AAAGTAAGGT GTGGGGATGA    3902

AGCTCTGGTT AAAGCCACTC TTTTGCTGTG CTCCGATCTC TTCTATCCGC TTCTGAGAGC    3962

AACCTTCATG ATTACAGCAA TTAATGTTTG CACAGAGCCC AGATTATACA GCAGTGGGTC    4022

ATTGTGCTTC ATTATTCAAG AATGAAGATA AAGACAAATA GAGGATTAGT AAAATATATT    4082

AAATGTGCAA TACCACTTAA ATGACTCTTA ATGTTTATAT TGAATTTCCA AAGCGATTAA    4142

ATAAAAAAGA GCTATTTTTT GTTATTGCCA AACAATATTT TTTGTATTTC TCTATTTTCA    4202

TAATGAGCAA ATAGCATCCT ATAAATCTGT TTATCTCTTC TTTGTAGTGT GTTTTCATAT    4262

AAATCCACAA GTAGAAAATC TTTTCATCTG TGGCATATTT CTATGACAAA TGCAAGATCT    4322

AGAAAAATTA AATGTTTGAT TATGCCATTT TGGAAATGCA TATTTACCAC CAAACCTATG    4382

TGACTGAATA ATGTCAAATA AAATTTTATG AATCATTTTA AAAAAAAAAA AAAAAGGGCG    4442

GCCGC                                                                4447
```

(2) INFORMATION FOR SEQ ID NO:4:

(i) SEQUENCE CHARACTERISTICS:
        (A) LENGTH: 1025 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Pro Val Leu Ser Lys Asp Val Ala Asp Ile Glu Ser Ile Leu
 1               5                  10                  15

Ala Leu Asn Pro Arg Thr Gln Ser His Ala Ala Leu His Ser Thr Leu
            20                  25                  30

Ala Lys Lys Leu Asp Lys Lys His Trp Lys Arg Asn Pro Asp Lys Asn
        35                  40                  45

Cys Phe His Cys Glu Lys Leu Glu Asn Asn Phe Gly Asp Ile Lys His
    50                  55                  60

Thr Thr Leu Gly Glu Arg Gly Ala Leu Arg Glu Ala Met Arg Cys Leu
65                  70                  75                  80

Lys Cys Ala Asp Ala Pro Cys Gln Lys Ser Cys Pro Thr His Leu Asp
                85                  90                  95

Ile Lys Ser Phe Ile Thr Ser Ile Ser Asn Lys Asn Tyr Tyr Gly Ala
               100                 105                 110

Ala Lys Met Ile Phe Ser Asp Asn Pro Leu Gly Leu Thr Cys Gly Met
           115                 120                 125
```

```
Val Cys Pro Thr Ser Asp Leu Cys Val Gly Cys Asn Leu Tyr Ala
    130                 135                 140

Thr Glu Glu Gly Ser Ile Asn Ile Gly Gly Leu Gln Gln Phe Ala Ser
145                 150                 155                 160

Glu Val Phe Lys Ala Met Asn Ile Pro Gln Ile Arg Asn Pro Cys Leu
                165                 170                 175

Pro Ser Gln Glu Lys Met Pro Glu Ala Tyr Ser Ala Lys Ile Ala Leu
            180                 185                 190

Leu Gly Ala Gly Pro Ala Ser Ile Ser Cys Ala Ser Phe Leu Ala Arg
        195                 200                 205

Leu Gly Tyr Ser Asp Ile Thr Ile Phe Glu Lys Gln Glu Tyr Val Gly
    210                 215                 220

Gly Leu Ser Thr Ser Glu Ile Pro Gln Phe Arg Leu Pro Tyr Asp Val
225                 230                 235                 240

Val Asn Phe Glu Ile Glu Leu Met Lys Asp Leu Gly Val Lys Ile Ile
                245                 250                 255

Cys Gly Lys Ser Leu Ser Glu Asn Glu Ile Thr Leu Asn Thr Leu Lys
            260                 265                 270

Glu Glu Gly Tyr Lys Ala Ala Phe Ile Gly Ile Gly Leu Pro Glu Pro
        275                 280                 285

Lys Thr Asp Asp Ile Phe Gln Gly Leu Thr Gln Asp Gln Gly Phe Tyr
    290                 295                 300

Thr Ser Lys Asp Phe Leu Pro Leu Val Ala Lys Ser Ser Lys Ala Gly
305                 310                 315                 320

Met Cys Ala Cys His Ser Pro Leu Pro Ser Ile Arg Gly Ala Val Ile
                325                 330                 335

Val Leu Gly Ala Gly Asp Thr Ala Phe Asp Cys Ala Thr Ser Ala Leu
            340                 345                 350

Arg Cys Gly Ala Arg Arg Val Phe Leu Val Phe Arg Lys Gly Phe Val
        355                 360                 365

Asn Ile Arg Ala Val Pro Glu Glu Val Glu Leu Ala Lys Glu Glu Lys
    370                 375                 380

Cys Glu Phe Leu Pro Phe Leu Ser Pro Arg Lys Val Ile Val Lys Gly
385                 390                 395                 400

Gly Arg Ile Val Ala Val Gln Phe Val Arg Thr Glu Gln Asp Glu Thr
                405                 410                 415

Gly Lys Trp Asn Glu Asp Glu Asp Gln Ile Val His Leu Lys Ala Asp
            420                 425                 430

Val Val Ile Ser Ala Phe Gly Ser Val Leu Arg Asp Pro Lys Val Lys
        435                 440                 445

Glu Ala Leu Ser Pro Ile Lys Phe Asn Arg Trp Asp Leu Pro Glu Val
    450                 455                 460

Asp Pro Glu Thr Met Gln Thr Ser Glu Pro Trp Val Phe Ala Gly Gly
465                 470                 475                 480

Asp Ile Val Gly Met Ala Asn Thr Thr Val Glu Ser Val Asn Asp Gly
                485                 490                 495

Lys Gln Ala Ser Trp Tyr Ile His Lys Tyr Ile Gln Ala Gln Tyr Gly
            500                 505                 510

Ala Ser Val Ser Ala Lys Pro Glu Leu Pro Leu Phe Tyr Thr Pro Val
        515                 520                 525

Asp Leu Val Asp Ile Ser Val Glu Met Ala Gly Leu Lys Phe Ile Asn
    530                 535                 540

Pro Phe Gly Leu Ala Ser Ala Ala Pro Thr Thr Ser Ser Ser Met Ile
```

-continued

```
545                 550                 555                 560
Arg Arg Ala Phe Glu Ala Gly Trp Gly Phe Ala Leu Thr Lys Thr Phe
                565                 570                 575
Ser Leu Asp Lys Asp Ile Val Thr Asn Val Ser Pro Arg Ile Val Arg
                580                 585                 590
Gly Thr Thr Ser Gly Pro Met Tyr Gly Pro Gly Gln Ser Ser Phe Leu
                595                 600                 605
Asn Ile Glu Leu Ile Ser Glu Lys Thr Ala Ala Tyr Trp Cys Gln Ser
                610                 615                 620
Val Thr Glu Leu Lys Ala Asp Phe Pro Asp Asn Ile Val Ile Ala Ser
625                 630                 635                 640
Ile Met Cys Ser Tyr Asn Lys Asn Asp Trp Met Glu Leu Ser Arg Lys
                645                 650                 655
Ala Glu Ala Ser Gly Ala Asp Ala Leu Glu Leu Asn Leu Ser Cys Pro
                660                 665                 670
His Gly Met Gly Glu Arg Gly Met Gly Leu Ala Cys Gly Gln Asp Pro
                675                 680                 685
Glu Leu Val Arg Asn Ile Cys Arg Trp Val Arg Gln Ala Val Gln Ile
                690                 695                 700
Pro Phe Phe Ala Lys Leu Thr Pro Asn Val Thr Asp Ile Val Ser Ile
705                 710                 715                 720
Ala Arg Ala Ala Lys Glu Gly Gly Ala Asp Gly Val Thr Ala Thr Asn
                725                 730                 735
Thr Val Ser Gly Leu Met Gly Leu Lys Ala Asp Gly Thr Pro Trp Pro
                740                 745                 750
Ala Val Gly Ala Gly Lys Arg Thr Thr Tyr Gly Gly Val Ser Gly Thr
                755                 760                 765
Ala Ile Arg Pro Ile Ala Leu Arg Ala Val Thr Thr Ile Ala Arg Ala
                770                 775                 780
Leu Pro Gly Phe Pro Ile Leu Ala Thr Gly Gly Ile Asp Ser Ala Glu
785                 790                 795                 800
Ser Gly Leu Gln Phe Leu His Ser Gly Ala Ser Val Leu Gln Val Cys
                805                 810                 815
Ser Ala Val Gln Asn Gln Asp Phe Thr Val Ile Gln Asp Tyr Cys Thr
                820                 825                 830
Gly Leu Lys Ala Leu Leu Tyr Leu Lys Ser Ile Glu Glu Leu Gln Gly
                835                 840                 845
Trp Asp Gly Gln Ser Pro Gly Thr Glu Ser His Gln Lys Gly Lys Pro
                850                 855                 860
Val Pro Arg Ile Ala Glu Leu Met Gly Lys Lys Leu Pro Asn Phe Gly
865                 870                 875                 880
Pro Tyr Leu Glu Gln Arg Lys Lys Ile Ile Ala Glu Glu Lys Met Arg
                885                 890                 895
Leu Lys Glu Gln Asn Ala Ala Phe Pro Pro Leu Glu Arg Lys Pro Phe
                900                 905                 910
Ile Pro Lys Lys Pro Ile Pro Ala Ile Lys Asp Val Ile Gly Lys Ala
                915                 920                 925
Leu Gln Tyr Leu Gly Thr Phe Gly Glu Leu Ser Asn Ile Glu Gln Val
                930                 935                 940
Val Ala Val Ile Asp Glu Glu Met Cys Ile Asn Cys Gly Lys Cys Tyr
945                 950                 955                 960
Met Thr Cys Asn Asp Ser Gly Tyr Gln Ala Ile Gln Phe Asp Pro Glu
                965                 970                 975
```

```
Thr His Leu Pro Thr Val Thr Asp Thr Cys Thr Gly Cys Thr Leu Cys
            980                 985                 990

Leu Ser Val Cys Pro Ile Ile Asp Cys Ile Arg Met Val Ser Arg Thr
            995                1000                1005

Thr Pro Tyr Glu Pro Lys Arg Gly Leu Pro Leu Ala Val Asn Pro Val
           1010                1015                1020

Cys
1025
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:5:

GCAAGGAGGG TTTGTCACTG                                                20

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:6:

CCGATTCCAC TGTAGTGTTA GCC                                             23

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:7:

TAACACTACA GTGGAATCGG                                                20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:8:

AAATCCAGGC AGAGCACGAG                                                20

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:9:

TGCTCGTGCT CTGCCTGGAT TTCC                                              24

(2) INFORMATION FOR SEQ ID NO:10:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:10:

ATTGAATGGT CATTGACATG AGAC                                              24

(2) INFORMATION FOR SEQ ID NO:11:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Cys Xaa Xaa Cys Xaa Xaa Cys Xaa Xaa Xaa Cys Xaa
1               5                   10

(2) INFORMATION FOR SEQ ID NO:12:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Cys Xaa Xaa Cys Xaa Xaa Cys Xaa Xaa Xaa Cys Pro
1               5                   10

(2) INFORMATION FOR SEQ ID NO:13:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Val Xaa Val Xaa Gly Xaa Gly Xaa Xaa Gly Xaa Xaa Xaa Ala Xaa Xaa
1               5                   10                  15
Ala

CLONING AND EXPRESSION OF CDNA FOR HUMAN DIHYDROPYRIMIDINE DEHYDROGENASE

This application is a divisional of and claims the benefit of U.S. application Ser. No. 08/304,309, filed Sep. 12, 1994 now U.S. Pat. No. 5,856,454, the disclosure of which is corporated by reference.

TECHNICAL FIELD OF THE INVENTION

The present invention relates to methods and compositions for detecting deficiencies in dihydropyrimidine dehydrogenase (DPD) levels in mammals, including humans. The methods and compositions are useful for identifying persons who are at risk of a toxic reaction to the commonly employed cancer chemotherapy agent 5-fluorouracil.

BACKGROUND OF THE INVENTION

5-Fluorouracil (5-FU) is commonly used in the treatment of cancers, including cancers of the breast, head, neck, and digestive system. The efficacy of 5-FU as a cancer treatment varies significantly among patients. Clinically significant differences in systemic clearance and systemic exposure of 5-FU are often observed. [Grem, J. L. In Chabner, B. A. and J. M. Collins (eds.), *Cancer Chemotherapy: Principles and Practice*, pp. 180–224, Philadelphia, Pa., Lippincott, 1990)]. Furthermore, 5-FU treatment is severely toxic to some patients, and has even caused death. [Fleming et al. (1993) *Eur. J. Cancer* 29A: 740–744; Thyss et al. (1986) *Cancer Chemother. Pharmacol.* 16: 64–66; Santini et al. (1989) *Br. J. Cancer* 59: 287–290; Goldberg et al. (1988) *Br. J. Cancer* 57: 186–189; Trump et al. (1991) *J. Clin. Oncol.* 9: 2027–2035; Au et al. (1982) *Cancer Res.* 42: 2930–2937].

Patients in whom 5-FU is severely toxic typically have low levels of dihydropyrimidine dehydrogenase (DPD) activity [Tuchman et al. (1985) *N. Engl. J. Med.* 313: 245–249; Diasio et al. (1988) *J. Clin. Invest.* 81: 47–51; Fleming et al. (1991) *Proc. Am. Assoc. Cancer Res.* 32: 179; Harris et al. (1991) *Cancer* (Phila.) 68: 499–501; Houyau et al. (1993) *J. Nat'l. Cancer Inst.* 85: 1602–1603; Lyss et al. (1993) *Cancer Invest.* 11: 239–240]. Dihydropyrimidine dehydrogenase (DPD, EC 1.3.1.2) is the principal enzyme involved in the degradation of 5-FU, which acts by inhibiting thymidylate synthase [Heggie et al. (1987) *Cancer Res.* 47: 2203–2206; Chabner et al. (1989) In DeVita et al. (eds.), *Cancer—Principles and Practice of Oncology*, pp. 349–395, Philadelphia, Pa., Lippincott; Diasio et al. (1989) *Clin. Pharmacokinet.* 16: 215–237; Grem et al., supra.]. The level of DPD activity also affects the efficacy of 5-FU treatments, as 5-FU plasma levels are inversely correlated with the level of DPD activity [ligo et al. (1988) *Biochem. Pharm.* 37: 1609–1613; Goldberg et al., supra.; Harris et al., supra.; Fleming et al., supra.]. In turn, the efficacy of 5-FU treatment of cancer is correlated with plasma levels of 5-FU.

In addition to its 5-FU degrading activity, DPD is also the initial and rate limiting enzyme in the three-step pathway of uracil and thymine catabolism, leading to the formation of β-alanine and β-aminobutyric acid, respectively [Wasternack et al. (1980) *Pharm. Ther.* 8: 629–665] DPD deficiency is associated with inherited disorders of pyrimidine metabolism, clinically termed thymine-uraciluria [Bakkeren et al. (1984) *Clin. Chim. Acta.* 140: 247–256]. Clinical symptoms of DPD deficiency include a nonspecific cerebral dysfunction, and DPD deficiency is associated with psychomotor retardation, convulsions, and epileptic conditions [Berger et al. (1984) *Clin. Chim. Acta* 141: 227–234; Wadman et al. (1985) *Adv. Exp. Med. Biol.* 165A: 109–114; Wilcken et al. (1985) *J. Inherit. Metab. Dis.* 8 (Suppl. 2): 115–116; van Gennip et al. (1989) *Adv. Exp. Med. Biol.* 253A: 111–118; Brockstedt et a. (1990) *J. Inherit. Metab. Dis.* 12: 121–124; Duran et al. (1991) *J. Inherit. Metab. Dis.* 14: 367–370]. Biochemically, patients having DPD deficiency have an almost complete absence of DPD activity in fibroblasts [Bakkeren et al., supra.] and in lymphocytes [Berger et al., supra.; Piper et al. (1980) *Biochim. Biophys. Acta* 633: 400–409]. These patients typically have a large accumulation of uracil and thymine in their cerebrospinal fluid [Bakkeren et al., supra.] and urine [Berger et al., supra.; Bakkeren et al., supra.; Brockstedt et al., supra.; Fleming et al. (1992) *Cancer Res.* 52: 2899–2902].

Familial studies suggest that DPD deficiency follows an autosomal recessive pattern of inheritance [Diasio et al., (1988) supra.]. Up to three percent of the general human population are estimated to be putative heterozygotes for DPD deficiency, as determined by enzymatic activity in lymphocytes [Milano and Eteinne (1994) *Pharmacogenetics* (in press)]. This suggests that the frequency of homozygotes for DPD deficiency may be as high as one person per thousand.

DPD has been purified from liver tissue of rats [Shiotani and Weber (1981) *J. Biol. Chem.* 256: 219–224; Fujimoto et al. (1991); *J. Nutr. Sci. Vitaminol.* 37: 89–98], pig [Podschun et al. (1989) *Eur. J. Biochem.* 185: 219–224], cattle [Porter et al. (1991) *J. Biol. Chem.* 266: 19988–19994], and human [Lu et al. (1992) *J. Biol. Chem.* 267: 1702–1709]. The pig enzyme contains flavins and iron-sulfur prosthetic groups and exists as a homodimer with a monomer Mr of about 107,000 [Podschun et al., supra.]. Since the enzyme exhibits a nonclassical two-site ping-pong mechanism, it appears to have distinct binding sites for NADPH/NADP and uracil/5, 6-dihydrouracil [Podschun et al. (1990) *J. Biol. Chem.* 265: 12966–12972]. An acid-base catalytic mechanism has been proposed for DPD [Podschun et al. (1993) *J. Biol. Chem.* 268: 3407–3413].

Because an undetected DPD deficiency poses a significant danger to a cancer patient who is being treated with 5-FU, a great need exists for a simple and accurate test for DPD deficiency. Such a test will also facilitate diagnosis of disorders that are associated with DPD deficiency, such as uraciluria. The present invention provides such a test, thus fulfilling these and other needs.

SUMMARY OF THE INVENTION

The claimed invention includes isolated nucleic acids that code for a dihydropyrimidine dehydrogenase (DPD) protein. Human and pig DPD cDNA sequences are claimed (Seq. ID No. 1 and Seq. ID No. 3, respectively), as are DPD nucleic acids that are capable of selectively hybridizing to the human or pig DPD cDNAs under stringent hybridization conditions. Oligonucleotide probes that are capable of selectively hybridizing, under stringent hybridizing conditions, to a human or pig DPD nucleic acid are also claimed. The invention also includes isolated nucleic acids that code for a DPD polypeptide that specifically binds to an antibody generated against an immunogen consisting of a human or pig DPD polypeptide having an amino acid sequence as depicted by Seq. ID No. 2 or Seq. ID No. 4.

Also claimed are methods for determining whether a patient is at risk of a toxic reaction to 5-fluorouracil (5-FU). The methods involve analyzing DPD DNA or mRNA in a sample from the patient to determine the amount of intact DPD nucleic acid. An enhanced risk of a toxic reaction to 5-fluorouracil is indicated by a decrease in the amount of intact DPD DNA or mRNA in the sample compared to the amount of DPD DNA or mRNA in a sample obtained from a patient known to not have a DPD deficiency, or by a defect in the DPD nucleic acid that results in an inadequate level of DPD activity.

The invention also includes methods for expressing recombinant DPD protein in a prokaryotic cell. The methods involve transfecting the cell with an expression vector comprising a promoter that is operably linked to a nucleic acid that encodes DPD, and incubating the cell in a medium that contains uracil to allow expression of the recombinant DPD protein.

Also claimed are expression vectors that utilize a nucleic acid that encodes DPD as a selectable marker. These selectable markers function in both eukaryotes and prokaryotes.

BRIEF DESCRIPTION OF THE FIGURES

FIGS. 1A–1B show the nucleotide sequence of the human DPYD cDNA.

FIGS. 2A–2B shows the nucleotide sequence of the pig DPYD cDNA.

FIG. 3 shows a comparison of the pig and human DPD cDNA deduced amino acid sequences. Only those amino acid residues of human DPD that differ from the pig sequences are shown below the pig DPD amino acid sequence. The following motifs relevant for catalytic activity are boxed: NADPH/NADP binding, FAD binding, uracil binding, and 4Fe-4S binding.

FIG. 4 shows the pedigree of a family used for a study of inheritance of DPD deficiency. Symbols are as follows: □ male, ○ female. Dotted symbols indicate intermediate DPD activity, a dashed square indicates high (normal) DPD activity, and ■ indicates undetectable DPD activity.

FIG. 6 is a schematic of the wild-type and mutant DPD cDNAs. Numbers above the cDNA graphical representation represent nucleotide positions. Start and stop codons are indicated.

DESCRIPTION OF THE SPECIFIC EMBODIMENTS

Definitions

Figure 5:
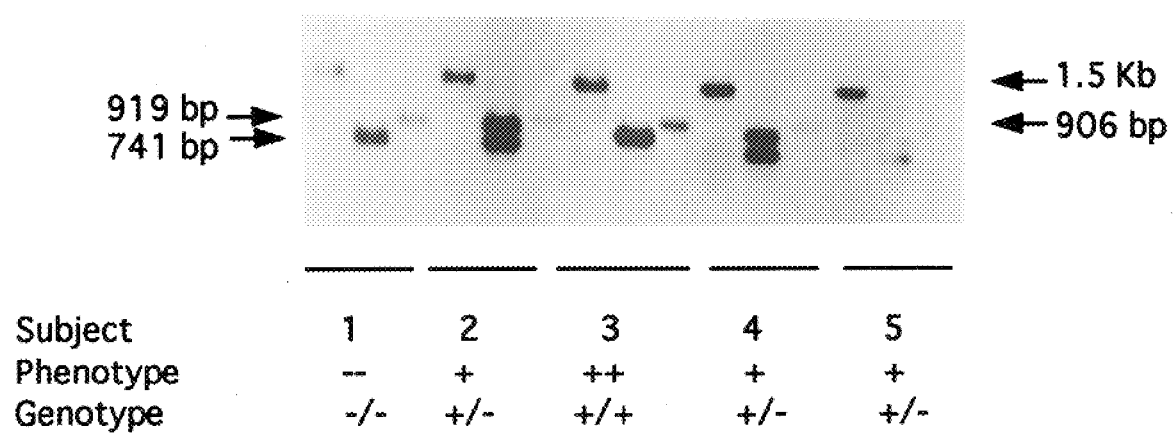
FIG. 5 shows a Southern blot of the products from reverse transcriptase PCR amplified cDNA for the subjects shown in FIG. 4. The 906 and 741 bp bands correspond to the wild-type and the deleted DPD cDNA fragments, respectively. "+" signifies the presence of the wild-type allele and "−" signifies the presence of the mutant allele.

Abbreviations for the twenty naturally occurring amino acids follow conventional usage. In the polypeptide notation used herein, the left-hand direction is the amino terminal direction and the right-hand direction is the carboxy-terminal direction, in accordance with standard usage and convention.

The term "nucleic acids," as used herein, refers to either DNA or RNA. Included are single or double-stranded polymers of deoxyribonucleotide or ribonucleotide bases. Self-replicating plasmids, infectious polymers of DNA or RNA and nonfunctional DNA or RNA are included. Unless specified otherwise, the left hand end of single-stranded polynucleotide sequences is the 5' end. The direction of 5' to 3' addition of ribonucleotides to nascent RNA transcripts is referred to as the transcription direction; sequence regions on the DNA strand having the same sequence as the RNA and which are 5' to the 5' end of the RNA transcript are referred to as "upstream sequences;" sequence regions on the DNA strand having the same sequence as the RNA and which are 3' to the 3' end of the RNA transcript are referred to as "downstream sequences."

"Nucleic acid probes" or "oligonucleotide probes" can be DNA or RNA fragments. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that, under appropriate hybridization conditions, hybridizes, duplexes or binds only to a particular target DNA or RNA sequence when the target sequences are present in a preparation of DNA or RNA. "Complementary" or "target" nucleic acid sequences refer to those nucleic acids that selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., (ed.) Greene Publishing and Wiley-Interscience, New York (1987).

The terms "stringent conditions" and "conditions of high stringency" refer to conditions under which a nucleic acid probe will hybridize substantially to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.2 molar at pH 7 and the temperature is at least about 60° C. for long sequences (e.g. greater than about 50 nucleotides) and at least about 42° C. for shorter sequences (e.g. 10 to 50 nucleotides). As other factors may significantly affect the stringency of hybridization, including, among others, base composition and size of the complementary strands, the presence of organic solvents and the extent of base mismatching, the combination of parameters is more important than the absolute measure of any one.

A nucleic acid is said to "encode" or "code for" a specific protein when the nucleic acid sequence comprises, in the proper order, codons for each of the amino acids of the protein or a specific subsequence of the protein. The nucleic acids include both the DNA strand that is transcribed into RNA and the RNA strand that is translated into protein. It is further understood that the invention includes nucleic acids that differ from the DPD sequences specifically disclosed herein in that particular codons are replaced by degenerate codons, so that the variant nucleic acid encodes a protein having the same amino acid sequence as that encoded by the specifically disclosed nucleic acids.

The phrase "isolated" or "substantially pure," when referring to nucleic acids that encode DPD, refers to nucleic acids that are sufficiently pure that the predominant nucleic acid species in the preparation is the desired DPD nucleic acid. Preferably, the DPD nucleic acids are more than 70% pure, more preferably greater than 90% pure, and most preferably greater than 95% pure.

The term "control sequence" refers to a DNA sequence or sequences that are capable, when properly attached to a desired coding sequence, of causing expression of the coding sequence. Such control sequences include at least promoters and, optionally, transcription termination signals. Additional factors necessary or helpful for expression can also be included. As used herein, "control sequences" simply refers to whatever DNA sequence signal that is useful to result in expression in the particular host used. Often, control sequences are utilized as an "expression cassette," in which the control sequences are operably linked to the nucleic acid that is to be expressed.

The term "operably linked" as used herein refers to a juxtaposition wherein the components are configured so as to perform their usual function. Thus, control sequences or promoters operably linked to a coding sequence are capable of effecting the expression of the coding sequence.

The term "vector" refers to nucleic acids that are capable of replicating in a selected host organism. The vector can replicate as an autonomous structure, or alternatively can integrate into the host cell chromosomes and thus replicate along with the host cell genome. Vectors include viral- or bacteriophage-based expression systems, autonomous self-replicating circular DNA (plasmids), and include both expression and nonexpression vectors. The term "plasmid" refers to an autonomous circular DNA molecule capable of replication in a cell, and includes both the expression and nonexpression types.

The phrase "recombinant protein" or "recombinantly produced protein" refers to a peptide or protein produced using recombinant DNA techniques. Host cells produce the recombinant protein because they have been genetically altered by the introduction of the appropriate nucleic acid that codes for the protein. Typically, the heterologous nucleic acid is introduced as part of an expression vector.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence can comprise a complete cDNA or gene sequence, such as the nucleic acid sequence of Seq. ID Nos. 1 or 3, or can be a subset of a larger sequence, for example, as a segment of a full-length cDNA or gene sequence.

Optimal alignment of sequences for aligning a comparison window can be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (*USA*) 85:2444, or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.).

The terms "substantial identity" or "substantial sequence identity" as applied to nucleic acids and as used herein denote a characteristic of a nucleotide sequence wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides. The percentage of sequence identity is calculated by comparing the reference sequence to the polynucleotide sequence, which may include deletions or additions which total 20 percent or less of the reference sequence over the window of comparison. The reference sequence may be a subset of a larger sequence, such as a segment or subsequence of the human DPD gene disclosed herein.

As applied to polypeptides, the terms "substantial identity" or "substantial sequence identity" mean that two peptide sequences, when optimally aligned, such as by the programs GAP or BESTFIT using default gap weights, share at least 80 percent sequence identity, preferably at least 90 percent sequence identity, more preferably at least 95 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions that are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a DPD polypeptide means a chemical composition that is essentially free of other cellular components. The DPD polypeptide is preferably in a homogeneous state, although it can be in either a dry form or in an aqueous solution. Purity and homogeneity are typically determined using analytical chemistry techniques such as polyacrylamide gel electrophoresis (PAGE) or high performance liquid chromatography (HPLC). A protein that is the predominant species present in a preparation is considered substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with," when referring to a protein or peptide, refers to a binding reaction that is determinative of the presence of the protein in the presence of a heterogeneous population of proteins and other biologics. Thus, under designated immunoassay conditions, the specified antibodies bind to a particular protein and do not bind in a significant amount to other proteins present in the sample. Obtaining an antibody that specifically binds to a particular protein may require screening. For example, antibodies raised to the human DPD protein immunogen with the amino acid sequence depicted in SEQ. ID No. 2 can be selected to obtain antibodies specifically immunoreactive with DPD proteins and not with other proteins. These antibodies recognize proteins that are homologous to the human DPD protein, such as DPD proteins from other mammalian species. A variety of immunoassay formats can be used to select antibodies specifically immunoreactive with a particular protein. For example, solid-phase enzyme-linked immunoassays (ELISAs) are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

DETAILED DESCRIPTION OF THE PREFERRED EMBODIMENT

The claimed invention provides compositions and methods that are useful for detecting deficient or diminished DPD activity in mammals, including humans. These methods and compositions are useful for identifying people who are at risk of a toxic reaction to the chemotherapy agent 5-fluorouracil. Methods and compositions for treating mammals who suffer from an insufficient level of DPD are also provided. Also included in the invention are methods for expressing high levels of DPD in prokaryotes, and selectable markers that function in both prokaryotes and eukaryotes.

The claimed methods and compositions are based on the discovery of an isolated cDNA that codes for human dihydropyrimidine dehydrogenase (DPD). A newly discovered cDNA that codes for pig DPD is also described. The human (SEQ. ID No. 1) and pig (SEQ. ID No. 3) DPD cDNA sequences are presented in FIGS. 1A–1B and 2A–2B, respectively. An alignment of the human and pig DPD deduced amino acid sequences is shown in FIG. 3. The nucleic acids of the invention are useful for determining whether a patient has an abnormal DPD gene, or whether the DPD gene in a patient is expressed an insufficient level. Either of these conditions can result in a DPD deficiency that can cause the patient to be susceptible to 5-FU toxicity. By detecting the DPD deficiency before treatment commences, the clinician can either adjust the dose of 5-FU downward, or can choose an alternative chemotherapy agent.

A. Description and Isolation of DPD Nucleic Acids

1. Description of DPD Nucleic Acids

The nucleic acids of the invention are typically identical to or show substantial sequence identity (determined as described above) to the nucleic acid sequences of SEQ ID No. 1 or SEQ ID No. 3. Nucleic acids encoding human DPD will typically hybridize to the nucleic acid sequence of SEQ ID Nos. 1 or 3 under stringent hybridization conditions as described herein.

Also claimed are isolated nucleic acids that code for a DPD polypeptide that specifically binds to an antibody generated against a specific immunogen, such as an immunogen that has of the amino acid sequence depicted by SEQ ID Nos. 2 or 4, or a specific subsequence of these polypeptides. To identify whether a nucleic acid encodes such a DPD polypeptide, an immunoassay is typically employed. Typically, the immunoassay will use a polyclonal or monoclonal antibody that was raised against the protein of SEQ ID Nos. 2 or 4. The antibody is selected to have low cross-reactivity against other (non-DPD) polypeptides, and any such cross- reactivity is removed by immunoadsorption prior to use in the immunoassay.

In order to produce antisera for use in an immunoassay, the DPD protein of SEQ ID Nos. 2 or 4 is isolated as described herein, for example, by recombinant expression. An inbred strain of mouse such as Balb/c is immunized with the DPD protein using a standard adjuvant, such as Freund's adjuvant, and a standard mouse immunization protocol (see Harlow and Lane, supra). Alternatively, a synthetic peptide derived from the amino acid sequences disclosed herein and conjugated to a carrier protein can be used an immunogen.

Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-DPD proteins, using a competitive binding immunoassay such as the one described in Harlow and Lane, supra, at pages 570–573. Three non-DPD proteins are used in this determination: the IRK protein [Kubo et al. (1993) *Nature* 362:127], the G-IRK protein [Kubo et al. (1993) *Nature* 364:802] and the ROM-K protein [Ho et al. (1993) *Nature* 362: 127]. These non-DPD proteins can be produced as recombinant proteins and isolated using standard molecular biology and protein chemistry techniques as described herein.

Immunoassays in the competitive binding format can be used for the crossreactivity determinations. For example, the DPD protein of SEQ ID Nos. 2 or 4 can be immobilized to a solid support. Proteins added to the assay compete with the binding of the antisera to the immobilized antigen. The ability of the above proteins to compete with the binding of the antisera against the immobilized protein is compared to the DPD protein of Seq. ID Nos. 2 or 4. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoadsorption with the above-listed proteins.

The immunoadsorbed and pooled antisera are then used in a competitive binding immunoassay as described above to determine whether a nucleic acid codes for a DPD polypeptide that specifically binds to an antibody generated against human or pig DPD polypeptide of SEQ ID No. 2 or 4, respectively. The second protein (the protein encoded by the nucleic acid of interest) and the immunogen protein (the human or pig DPD protein of SEQ ID Nos. 2 or 4) are compared for their ability to inhibit binding of the antiserum to immobilized human or pig DPD polypeptide. In order to make this comparison, the two proteins are each assayed at a wide range of concentrations to determine the amount of each protein required to inhibit the binding of the antisera to the immobilized protein by 50%. If the amount of the second protein required is less than 10 times the amount of the human DPD protein of SEQ ID No. 2 that is required, then the second protein is said to specifically bind to an antibody generated to an immunogen consisting of the human DPD protein of SEQ ID No. 2. Similarly, the second protein is said to specifically bind to an antibody generated against an immunogen consisting of the pig DPD protein of SEQ ID No. 4 if the amount of second protein required to block antiserum binding by 50% is ten times or less than the amount of pig DPD protein required.

2. Isolation of DPD Nucleic Acids

The DPD nucleic acid compositions of this invention, whether cDNA, genomic DNA, RNA, or a hybrid of the various combinations, may be isolated from natural sources or may be synthesized in vitro. The nucleic acids claimed can be present in transformed or transfected whole cells, in a transformed or transfected cell lysate, or in a partially purified or substantially pure form.

Techniques for manipulating the DPD and other nucleic acids, such as those techniques used for subcloning the nucleic acids into expression vectors, labelling probes, nucleic acid hybridization, and the like are described generally in Sambrook et al., *Molecular Cloning—A Laboratory Manual* (2nd Ed.), Vol. 1–3, Cold Spring Harbor Laboratory, Cold Spring Harbor, N.Y., 1989, which is incorporated herein by reference. This manual is hereinafter referred to as "Sambrook."

Various methods for isolating the DPD nucleic acids are available. For example, one can isolate DNA from a genomic or cDNA library by using labelled oligonucleotide probes that have nucleotide sequences that are complementary to the human and pig DPD gene sequences disclosed herein (SEQ. ID Nos. 1 and 3, respectively). One can use full-length probes or oligonucleotide probes that are based on specific subsequences of these genes. Probes are discussed more fully below. One can use such probes directly in hybridization assays to identify nucleic acids that code for DPD, or one can use amplification methods such as PCR to isolate DPD nucleic acids.

Methods for making and screening cDNA libraries are well known. See, e.g., Gubler, U. and Hoffman, B. J. (1983) Gene 25: 263–269 and Sambrook, supra. Briefly, to prepare a cDNA library for the purpose of isolating a DPD cDNA, one isolates mRNA from tissue that expresses DPD. Liver is a particularly useful tissue for this purpose, as are peripheral blood lymphocytes.

Most other cells also likely produce DPD due to its critical role in pyrimidine degradation and β-alanine synthesis. cDNA is then prepared from the mRNA using standard techniques and ligated into a recombinant vector. The vector is transfected into a recombinant host for propagation, screening and cloning.

Methods for preparing genomic libraries are also well known to those of skill in the art. See, e.g., Sambrook, supra. Typically, one can prepare a genomic library by extracting DNA from tissue and either mechanically shearing or enzymatically digesting the DNA to yield fragments of about 12–20 kb, or longer if a cosmid is used as the cloning vector. Fragments of the desired size are purified by density gradient centrifugation or gel electrophoresis. The fragments are then cloned into suitable cloning vectors, such as bacteriophage lambda vectors or cosmids. If phage or cosmids are used, one then packages the DNA in vitro, as described in Sambrook, supra. Recombinant phage or cosmids are analyzed by plaque hybridization as described in Benton and Davis, (1977) *Science* 196: 180–182. Colony hybridization is carried out as generally described in Grunstein et al. (1975) *Proc. Natl. Acad. Sci. USA*. 72: 3961–3965.

Standard techniques are used to screen the cDNA or genomic DNA libraries to identify those vectors that contain a nucleic acid that encodes a human or mammalian DPD. For example, Southern blots are utilized to identify those library members that hybridize to nucleic acid probes derived from the human or pig DPD nucleotide sequences shown in FIGS. 1A–1B and 2A–2B, respectively. See, e.g., Sambrook, supra.

Alternatively, one can prepare DPD nucleic acids by using any of various methods of amplifying target sequences, such as the polymerase chain reaction. For example, one can use polymerase chain reaction (PCR) to amplify DPD nucleic acid sequences directly from mRNA, from cDNA or genomic DNA, or from genomic DNA libraries or cDNA libraries. Briefly, to use PCR to isolate the DPD nucleic acids from genomic DNA, one synthesizes oligonucleotide primer pairs that are complementary to the 3' sequences that flank the DNA region to be amplified. One can select primers to amplify the entire region that codes for a full-length DPD polypeptide, or to amplify smaller DNA segments that code for part of the DPD polypeptide, as desired. Suitable primer pairs for amplification of the human DPYD gene are shown in Table 1 and are listed as SEQ ID Nos. 5 and 6, 7 and 8, 9 and 10. Polymerase chain reaction is then carried out using the two primers. See, e.g., PCR Protocols. *A Guide to Methods and Applications*. (Innis, M, Gelfand, D., Sninsky, J. and White, T., eds.), Academic Press, San Diego (1990). Amplified fragments can be used as hybridization probes to identify other DPD nucleic acids, such as those from organisms other than human and pig.

Other methods known to those of skill in the art can also be used to isolate DNA encoding the DPD polypeptides. See, e.g., Sambrook, supra., for a description of other techniques that are useful for isolating DNA that codes for specific polypeptides.

B. Diagnostic Methods: Detection of DPD Deficiency by Nucleic Acid Detection To permit the clinician to determine whether a patient has diminished or deficient DPD activity, and thus an enhanced risk of a toxic reaction to 5-FU, the present invention provides methods and reagents for detecting DNA and RNA molecules that code for DPD. These methods permit one to detect DPD deficiency in a patient whether the deficiency is due to a deleted DPD gene (DPYD), a DPD gene that is expressed at a lower than normal rate, or a missense or nonsense mutation that results in an abnormal DPD polypeptide. If any of these tests indicate that the patient has a DPD deficiency, the clinician should exercise extreme caution in using 5-FU as a chemotherapy agent. These methods are also suitable for diagnosing other disorders that are caused by DPD nucleic acid deficiency, such as thymine uraciluria.

1. Oligonucleotide Probes

One aspect of the invention is nucleic acid probes that are useful for detecting the presence or absence of DPD nucleic acids in a sample from a human or other mammal. Typically, oligonucleotides are used, although longer fragments that comprise most or all of a DPD gene are also suitable. The claimed probes are specific for human or pig DPD genes. Oligonucleotide probes are generally between about 10 and 100 nucleotides in length, and are capable of selectively hybridizing, under stringent hybridizing conditions, to a target region, a specific subsequence of a DPD nucleic acid. The probes selectively hybridize to DPD nucleic acids, meaning that under stringent hybridization conditions the probes do not substantially hybridize to non-DPD nucleic acids (less than 50% of the probe molecules hybridize to non-DPD nucleic acids). One of skill will recognize that oligonucleotide probes complementary to specific subsequences of the target regions, but not to the entire target region, will also function in the claimed assays so long as such probes selectively hybridize to the target regions.

Alternatively, the oligonucleotide probe can comprise a concatemer that has the formula [X-Y-Z]n, wherein:

a) X is a sequence of 0 to 100 nucleotides or nucleotide analogs that are not complementary to a DPD nucleic acid;

b) Y is a sequence of 10 to 100 nucleotides or nucleotide analogs that are capable of hybridizing under stringent hybridizing conditions to a DPD nucleic acid;

c) Z is a sequence of nucleotides the same as or different from X, such that nucleotides or nucleotide analogs are not complementary to a DPD nucleic acid; and d) n is 1–500, or more and, where n is greater than 1, Y can be the same or different sequences of nucleotides having the indicated hybridization capability. The probe can be free or contained within a vector sequence (e.g., plasmids or single stranded DNA).

The degree of complementarity (homology) required for detectable binding with the DPD nucleic acids will vary in accordance with the stringency of the hybridization medium and/or wash medium. The degree of complementarity will optimally be 100 percent; however, it should be understood that minor variations in the DPD nucleic acids may be compensated for by reducing the stringency of the hybridization and/or wash medium as described below. Thus, despite the lack of 100 percent complementarity under reduced conditions of stringency, functional probes having minor base differences from their DPD nucleic acid targets are possible. Therefore, under hybridization conditions of reduced stringency, it may be possible to modify up to 60% of a given oligonucleotide probe while maintaining an acceptable degree of specificity. In addition, analogs of nucleosides may be substituted within the probe for naturally occurring nucleosides. This invention is intended to embrace these species when referring to polynucleic acid probes.

Suitable oligonucleotide probes include synthetic oligonucleotides, cloned DNA fragments, PCR products, and RNA molecules. The nature of the probe is not important, provided that it hybridizes specifically to DPD nucleic acids, and not to other nucleic acids under stringent hybridization conditions.

To obtain large quantities of DNA or RNA probes, one can either clone the desired sequence using traditional cloning methods, such as described in Sambrook et al., *Molecular Cloning: A Laboratory Manual*, Cold Spring Harbor, N.Y., 1989, or one can produce the probes by chemical synthesis using commercially available DNA synthesizers. An example of cloning would involve insertion of all or part of the cDNA for the human or pig DPD gene into a replication vector, such as pBR322, M13, or into a vector containing the SP6 promotor (e.g., for generation of single-stranded DPD RNA using SP6 RNA polymerase), and transformation of a bacterial host. The probes can be purified from the host cell by lysis and nucleic acid extraction, treatment with selected restriction enzymes, and further isolation by gel electrophoresis.

Oligonucleotide probes can be chemically synthesized using commercially available methods and equipment. For example, the solid phase phosphoramidite triester method first described by Beaucage and Carruthers [(1981) *Tetrahedron Lett.* 22: 1859–1862] is suitable. This method can be used to produce relatively short probes of between 10 and 50 bases. The triester method described by Matteucci et al. [(1981) *J. Am. Chem. Soc.*, 103:3185] is also suitable for synthesizing oligonucleotide probes. Conveniently, one can use an automated oligonucleotide synthesizer such as the Model 394 DNA/RNA Synthesizer from Applied Biosystems (Foster City, Calif.) using reagents supplied by the same company.

After synthesis, the oligonucleotides are purified either by native acrylamide gel electrophoresis or by anion-exchange HPLC as described in, for example, Pearson and Regnier (1983) *J. Chrom.* 255: 137–149. The sequence of the synthetic oligonucleotide can be verified using the chemical degradation method of Maxam, A. M. and Gilbert, W. (1980) In Grossman, L. and Moldave, D., eds. Academic Press, New York, *Methods in Enzymology*, 65:499–560.

Probes can be comprised of the natural nucleotides or known analogs of the natural nucleotides, including those modified to bind labeling moieties. Oligonucleotide probes that comprise thionucleotides, and thus are resistant to nuclease cleavage, are also suitable. One can use probes that are the full length of the DPD coding regions, or probes that hybridize to a specific subsequence of a DPD gene. Shorter probes are empirically tested for specificity. Preferably, nucleic acid probes are 15 nucleotides or longer in length, although oligonucleotide probe lengths of between about 10 and 100 nucleotides or longer are appropriate. Sambrook, supra. describes methods for selecting nucleic acid probe sequences for use in nucleic acid hybridization.

For purposes of this invention, the probes are typically labelled so that one can detect whether the probe has bound to a DPD nucleic acid. Probes can be labeled by any one of several methods typically used to detect the presence of hybrid polynucleotides. The most common method of detection is the use of autoradiography using probes labeled with $^3H$, $^{125}I$, $^{35}S$, $^{14}C$, $^{32}P$, or the like. The choice of radioactive isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The choice of label dictates the manner in which the label is bound to the probe. Radioactive probes are typically made using commercially available nucleotides containing the desired radioactive isotope. The radioactive nucleotides can be incorporated into probes, for example, by using DNA synthesizers, by nick translation or primer extension with DNA polymerase 1, by tailing radioactive nucleotides to the 3' end of probes with terminal deoxynucleotidyl transferase, by incubating single-stranded M13 plasmids having specific inserts with the Klenow fragment of DNA polymerase in the presence of radioactive deoxynucleotides, dNTP, by transcribing from RNA templates using reverse transcriptase in the presence of radioactive deoxynucleotides, dNTP, or by transcribing RNA from vectors containing specific RNA viral promoters (e.g., SP6 promoter) using the corresponding RNA polymerase (e.g., SP6 RNA polymerase) in the presence of radioactive ribonucleotides rNTP.

The probes can be labeled using radioactive nucleotides in which the isotope resides as a part of the nucleotide molecule, or in which the radioactive component is attached to the nucleotide via a terminal hydroxyl group that has been esterified to a radioactive component such as inorganic acids, e.g., $^{32}P$ phosphate or $^{14}C$ organic acids, or esterified to provide a linking group to the label. Base analogs having nucleophilic linking groups, such as primary amino groups, can also be linked to a label.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, as described in Renz. M., and Kurz, K. (1984) A Colorimetric Method for DNA Hybridization. *Nucl. Acids Res.* 12: 3435–3444. Synthetic oligonucleotides have been coupled directly to alkaline phosphatase [Jablonski, E., et al. (1986) Preparation of Oligodeoxynucleotide-Alkaline Phosphatase Conjugates and Their Use as Hybridization Probes. *Nucl. Acids Res.* 14: 6115–6128; and Li P., et al. (1987) Enzyme-linked Synthetic Oligonucleotide probes: Non-Radioactive Detection of Enterotoxigenic *Escherichia coli* in Faeca Specimens. *Nucl. Acids Res.* 15: 5275–5287].

Enzymes of interest as labels will typically be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol.

The oligonucleotide or polynucleotide acid probes of this invention can be included in a kit which can be used to rapidly determine the level of DPD DNA or mRNA in cells of a human or other mammalian sample. The kit includes all components necessary to assay for the presence of the DPD DNA or mRNA. In the universal concept, the kit includes a stable preparation of labeled probes specific for DPD nucleic acids, hybridization solution in either dry or liquid form for the hybridization of target and probe polynucleotides, as well as a solution for washing and removing undesirable and nonduplexed polynucleotides, a substrate for detecting the labeled duplex, and optionally an instrument for the detection of the label.

The probe components described herein include combinations of probes in dry form, such as lyophilized nucleic acid or in precipitated form, such as alcohol precipitated nucleic acid or in buffered solutions. The label can be any of the labels described above. For example, the probe can be biotinylated using conventional means and the presence of a biotinylated probe can be detected by adding avidin conjugated to an enzyme, such as horseradish peroxidase, which can then be contacted with a substrate which, when reacted with peroxidase, can be monitored visually or by instrumentation using a calorimeter or spectrophotometer. This labeling method and other enzyme-type labels have the advantage of being economical, highly sensitive, and relatively safe compared to radioactive labeling methods. The various reagents for the detection of labeled probes and other miscellaneous materials for the kit, such as instructions, positive and negative controls, and containers for conducting, mixing, and reacting the various components, would complete the assay kit.

2. Assays for Detecting DPD Nucleic Acid Deficiency

One embodiment of the invention provides assays for determining whether a patient is at risk of a toxic reaction to 5-fluorouracil, or suffers from a condition that is caused by inadequate levels of DPD (such as thymine uraciluria). The assay methods involve determining whether the patient is deficient in DPD nucleic acids. A deficiency can arise if the patient is lacking all or part of one or both copies of the DPD gene, or if the DPD gene is not expressed in the appropriate cells of the patient. Another potential cause of DPD deficiency that is detectable using the claimed invention is a nonsense or missense mutation in the DPD gene that results in an abnormal DPD polypeptide.

Assay test protocols for use in this invention are those of convention in the field of nucleic acid hybridization, and include both single phase, where the target and probe polynucleic acids are both in solution, and mixed phase hybridizations, where either the target or probe polynucleotides are fixed to an immobile support. The assay test protocols are varied and are not to be considered a limitation of this invention. A general review of hybridization can be had from a reading of *Nucleic Acid Hybridization: A Practical Approach*, Hames and Higgins, eds., IRL Press, 1985; and *Hybridization of Nucleic Acids Immobilized on Solid Supports*, Meinkoth and Wah (1984) *Analytical Biochemistry*, pp. 238, 267–284. Mixed phase hybridizations are preferred.

One potential cause of DPD deficiency is a deletion of all or part of one or more copies of the DPD gene in a patient's chromosomal DNA. To determine whether a patient lacks a gene that codes for DPD, the clinician can employ a Southern blot or other means suitable for detecting the presence of a specific nucleotide sequence in genomic DNA. A variety of methods for specific DNA and RNA measurement using nucleic acid hybridization techniques are known to those of skill in the art. See, e.g., Sambrook, supra. Briefly, the procedure for a Southern blot is as follows. Genomic DNA is isolated from a sample obtained from the patient. One can obtain DNA from almost any cellular tissue of the patient. The DNA is digested using one or more restriction enzymes, after which it is size-fractionated by electrophoresis through an agarose slab gel. The DNA is then immobilized by transfer from the gel to a membrane (commonly nylon or nitrocellulose).

If all or part of the DPD gene is missing from the patient's genomic DNA, the probe will not hybridize to the genomic DNA, or else will hybridize to a different-sized restriction fragment compared to the wild-type DPD gene. If a patient is heterozygous at the DPD locus, the clinician will observe either a reduced hybridization signal compared to wild-type (probe region deleted from one of the two alleles) or hybridization to two different-sized restriction fragments (part of one DPD gene deleted). If a sample from a patient lacks a gene that codes for DPD, the clinician should exercise extreme caution in using 5-FU as chemotherapy. A patient who is missing all or part of one or both DPD genes (e.g., either a heterozygote or homozygote for a defective DPD gene) is at risk of 5-FU toxicity or conditions such as thymine uraciluria that are due to inadequate levels of DPD activity.

DPD deficiency that results in 5-FU toxicity or thymine uraciluria might also result from insufficient DPD mRNA levels. The Northern blot is a particularly useful method for detecting DPD mRNA levels. By detecting DPD mRNA levels, rather than detecting the presence of the DPD gene, Northern blots permit quantitation of DPD gene expression. This facilitates identification of patients who are DPD deficient for any of several reasons. A homozygote in which both DPD alleles are deleted will produce no DPD mRNA, while a heterozygote will generally have an intermediate level of DPD mRNA compared to a patient who is homozygous wild type. A Northern blot also allows the clinician to identify patients who, although they carry DPD genes, have a lower than normal level of DPD gene expression. Such patients are also at risk of 5-FU toxicity and thymine uraciluria.

Suitable samples for detection of DPD mRNA include any cells from the patient that express the DPD gene. Preferably, the cells will be obtained from a tissue that has high levels of DPD activity. In humans, the liver and lymphocytes generally have the highest DPD activity, with other tissues having less activity [Naguib et al. (1985) *Cancer Res.* 45: 5405–5412]. Because lymphocytes are much easier to isolate from a patient than liver cells, lymphocytes are a preferred sample for detecting DPD mRNA according to the claimed invention. However, one can also detect DPD mRNA in other cell types, such as fibroblasts.

Suitable methods for Northern blots are described in, for example, Sambrook, supra. and Chomczynski and Sacchi (1987) *Anal. Biochem.* 162: 156–159. Briefly, RNA is isolated from a cell sample using an extraction solution that releases the RNA from the cells while preventing degradation of the RNA. A commonly-used extraction solution contains a guanidinium salt. The RNA is purified from the extraction solution, such as by phenol-chloroform extraction followed by ethanol precipitation. Optionally, one can separate the mRNA from ribosomal RNA and transfer RNA by oligo-dT cellulose chromatography, although such purification is not required to practice the claimed invention. The RNA is then size-fractionated by electrophoresis, after which the RNA is transferred from the gel to a nitrocellulose or nylon membrane. Labeled probes are used to ascertain the presence or absence of DPD-encoding mRNA.

If a sample from a patient has an insufficient amount of DPD nucleic acids, the patient is at risk of a toxic reaction to 5-FU, or is likely to suffer from thymine uraciluria or a related condition. Generally, an insufficient amount of DPD nucleic acids is less than about 70% of the normal amount of DPD nucleic acid, where "normal" refers to the amount of DPD nucleic acid found in the same amount of DNA or RNA from a sample that is not known to have a DPD deficiency. More typically, an amount of DPD that is less than about 50% of normal is indicative of an enhanced risk of 5-FU toxicity or thymine uraciluria.

Yet another potential cause of DPD deficiency in a patient is a missense or nonsense mutation in the DPD gene, or a mutation that interferes with mRNA processing. Our invention allows the clinician to detect these mutations. By choosing a probe that hybridizes to a mutant DPD gene, but not to the wild-type DPD gene (or vice versa), one can determine whether the patient carries an abnormal DPD gene that may result in inadequate expression of the DPD gene, or expression of an abnormal DPD enzyme that has less activity than the wild-type enzyme.

A variety of nucleic acid hybridization formats in addition to Northern and Southern blots are known to those skilled in the art. For example, common formats include sandwich assays and competition or displacement assays. Hybridization techniques are generally described in "Nucleic Acid Hybridization, A Practical Approach," Hames, B. D. and Higgins, S. J. (eds.), IRL Press, 1985; Gall and Pardue (1969) Proc. Natl Acad. Sci. USA. 63: 378–383; and John et al. (1969) Nature 223: 582–587. These assays are sometimes preferred over classical Northern and Southern blots because of their greater speed and simplicity.

Sandwich assays are commercially useful hybridization assays for detecting or isolating nucleic acid sequences. These assays are easily automated, which results in a more cost-effective and sometimes more accurate assay. Sandwich assays utilize a "capture" nucleic acid that is covalently linked to a solid support, and a labelled "signal" nucleic acid that is in solution. The clinical sample provides the target nucleic acid. The "capture" nucleic acid and "signal" nucleic acid probe each hybridize to the target nucleic acid to form a "sandwich" hybridization complex. To be effective, the signal nucleic acid cannot hybridize to the capture nucleic acid.

One embodiment of this invention embraces a kit that utilizes the concept of the sandwich assay. This kit includes a first component for the collection of samples from patients, vials for containment, and buffers for the dispersement and lysis of the sample. A second component contains media in either dry or liquid form for the hybridization of target and probe polynucleotides, as well as for the removal of undesirable and nonduplexed forms by washing. A third component includes a solid support upon which is fixed or to which is conjugated unlabeled nucleic acid probe(s) that is(are) complementary to a DPD nucleic acid. In the case of multiple target analysis more than one capture probe, each specific for its own DPD nucleic acid target region, will be applied to different discrete regions of the dipstick. A fourth component contains labeled probe that is complementary to a second and different region of the same DPD nucleic acid strand to which the immobilized, unlabeled nucleic acid probe of the third component is hybridized.

No matter which assay format is employed, labelled signal nucleic acids are typically used to detect hybridization. Complementary nucleic acids or signal nucleic acids can be labelled by any one of several methods typically used to detect the presence of hybridized polynucleotides, as described above. The most common method of detection is the use of autoradiography with $^3$H, $^{125}$I, $^{35}$S, $^{14}$C, or $^{32}$P-labelled probes or the like. Other labels include ligands which bind to labelled antibodies, fluorophores, chemiLuminescent agents, enzymes, and antibodies which can serve as specific binding pair members for a labelled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal. The label can also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. [Tijssen, P., "Practice and Theory of Enzyme Immunoassays," Laboratory Techniques in Biochemistry and Molecular Biology, Burdon, R. H., van Knippenberg, P. H., Eds., Elsevier (1985), pp. 9–20].

The sensitivity of the hybridization assays can be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems. Amplification methods permit one to detect the presence or absence of DPD nucleic acids using only a very small sample. Furthermore, amplification methods are especially amenable to automation.

One preferred method for detecting DPD deficiency is reverse transcriptase PCR (RT-PCR). Briefly, this method involves extracting RNA from the sample being analyzed, making a cDNA copy of the mRNA using an oligo-dT primer and reverse transcriptase, and finally amplifying part or all of the cDNA by PCR. For primers, one can use oligonucleotide primers that are complementary to the 5' and 3' sequences that flank the DNA region to be amplified. One can select primers to amplify the entire region that codes for a full-length DPD polypeptide, or to amplify smaller DNA segments that code for part of the DPD polypeptide, as desired. For human DPD analysis, suitable pairs of primers include: SEQ. ID Nos. 5 and 6, SEQ. ID Nos. 7 and 8, and SEQ. ID Nos. 9 and 10. A detailed example of RT-PCR analysis as used for detection of DPD deficiency is presented in Example 4 below.

An alternative means for determining the level at which a DPD gene is expressed is in situ hybridization. In situ hybridization assays are well known and are generally described in Angerer et al. (1987) Methods Enzymol. 152: 649–660. In an in situ hybridization assay, cells are fixed to a solid support, typically a glass slide. If DNA is to be probed, the cells are denatured with heat or alkali. The cells are then contacted with a hybridization solution at a moderate temperature to permit annealing of labeled probes specific to DPD-encoding nucleic acids. The probes are preferably labelled with radioisotopes or fluorescent labels.

C. Expression of Recombinant Dihydropyrimidine Dehydroqenase

The present invention also provides methods for expressing recombinant dihydropyrimidine dehydrogenase DPD). These methods involve cloning the claimed isolated DPD cDNA into an appropriate expression vector, transforming the expression vector into a host cell, and growing the host cells under conditions that lead to expression ot the DPD cDNA. Numerous expression systems are suitable for expression of cDNA encoding DPD. Because these basic techniques are known to those of skill in the art, no attempt is made here to describe in detail the various basic methods known for the expression of proteins in prokaryotes or eukaryotes.

In brief summary, the expression of natural or synthetic nucleic acids encoding DPD will typically be achieved by operably linking a DPD-encoding cDNA to a promoter that functions in the host cell of choice. Either constitutive or inducible promoters are suitable. This "expression cassette" is typically incorporated in an expression vector. The vectors contain regulatory regions that cause the vector to replicate autonomously in the host cell, or else the vector can replicate by becoming integrated into the genomic DNA of the host cell. Suitable vectors for both prokaryotes and eukaryotes are known to those of skill in the art. Typical expression vectors can also contain transcription and translation terminators, translation initiation sequences, and enhancers that are useful for regulating the amount of DPD expression. To obtain high level expression of a cloned gene, such as those polynucleotide sequences encoding DPD, it is desirable to construct expression vectors that contain, at minimum, a strong promoter to direct transcription, a ribosome binding site for translational initiation, and a transcription/translation terminator. Expression vectors often contain control elements that permit the vector to replicate in both eukaryotes and prokaryotes, as well as selectable markers that function in each. See, e.g., Sambrook, supra., for examples of suitable expression vectors.

1. Expression in Eukarvotes

A variety of eukaryotic expression systems such as yeast, insect cell lines, bird, fish, and mammalian cells, are known to those of skill in the art. Eukaryotic systems, including yeast, mammalian, and insect, suitable for expressing DPD are discussed briefly below.

Synthesis of heterologous proteins in yeast is well known. *Methods in Yeast Genetics*, Sherman, F., et al., Cold Spring Harbor Laboratory, (1982) is a well recognized work describing the various methods available to produce the protein in yeast. Suitable vectors for expression in yeast usually have expression control sequences, such as promoters, including 3-phosphoglycerate kinase or other glycolytic enzymes, and an origin of replication, termination sequences and the like as desired. For instance, suitable vectors are described in the literature (Botstein, et al., 1979, *Gene*, 8:17–24; Broach, et al., 1979, *Gene*, 8:121–133). Several commercial manufacturers of molecular biology reagents sell expression vectors that are suitable for use in different eukaryotic host cells [See, e.g., product catalogs from Stratagene Cloning Systems, La Jolla Calif.; Clontech Laboratories, Palo Alto Calif.; Promega Corporation, Madison Wis.]. These vectors are used as directed by the manufacturers except for the modifications described below that are necessary for expression of DPD.

Two procedures are commonly used to transform yeast cells. The first method involves converting yeast cells into protoplasts using an enzyme such as zymolyase, lyticase or glusulase. The protoplasts are then exposed to DNA and polyethylene glycol (PEG), after which the PEG-treated protoplasts are then regenerated in a 3% agar medium under selective conditions. Details of this procedure are given in the papers by Beggs (1978) *Nature* (London) 275: 104–109 and Hinnen et al. (1978) *Proc. Natl. Acad. Sci. USA* 75: 1929–1933. The second procedure does not involve removal of the cell wall. Instead the cells are treated with lithium chloride or acetate and PEG and put on selective plates [Ito et al. (1983) *J. Bact.* 153: 163–168].

The DPD polypeptides, once expressed, can be isolated from yeast by lysing the cells and applying standard protein isolation techniques to the lysates. The monitoring of the purification process can be accomplished by using Western blot techniques, or radioimmunoassay or other standard immunoassay techniques.

Higher eukaryotes are also suitable host cells for expression of recombinant DPD. Again, previously described methods are suitable, except that the modifications described below are necessary for efficient expression of DPD. Expression vectors for use in transforming, for example, mammalian, insect, bird, and fish cells are known to those of skill in the art.

Mammalian cells are illustrative of the techniques used for expression of DPD in eukaryotic cells. Mammalian cells typically grow in the form of monolayers of cells, although mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSV tk (thymidine kinase) promoter or pgk (phosphoglycerate kinase) promoter), an enhancer [Queen et al. (1986) *Immunol. Rev.* 89:49], and necessary processing information sites, such as ribosome binding sites, RNA splice sites, polyadenylation sites (e.g., an SV40 large T Ag poly A addition site), and transcriptional terminator sequences. Other animal cells useful for production of recombinant DPD are available, for instance, from the American Type Culture Collection Catalogue of Cell Lines and Hybridomas (7th edition, 1992), as well as from various commercial manufacturers of molecular biology reagents.

Insect cells are another eukaryotic system that is useful for expressing recombinant DPD protein. Appropriate vectors for expressing recombinant DPD in insect cells are usually derived from the SF9 baculovirus. Suitable insect cell lines include mosquito larvae, silkworm, armyworm, moth and Drosophila cell lines such as a Schneider cell line [See, Schneider J. (1987) *Embryol. Exp. Morphol.* 27:353–365].

Higher eukaryotic host cells, such as mammalian and insect cells, are rendered competent for transformation by various means. There are several wellknown methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and micro-injection of the DNA directly into the cells.

The transformed cells are cultured by means well known in the art. *Biochemical Methods in Cell Culture and Virology*, Kuchler, R. J., Dowden, Hutchinson and Ross, Inc (1977). The expressed polypeptides are isolated from cells grown as suspensions or as monolayers. The DPD polypeptides are recovered by well known mechanical, chemical or enzymatic means.

2. Expression in Prokaryotes

A variety of prokaryotic expression systems can be used to express recombinant DPD. Examples of suitable host cells include *E. coli*, Bacillus, Streptomyces, and the like. For each host cell, one employs an expression plasmids that contains appropriate signals that direct transcription and translation in the chosen host organism. Such signals typically include a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, C. (1984) *J. Bacteriol.* 158: 1018–1024 and the leftward promoter of phage lambda (p$\lambda$) as described by Herskowitz and Hagen (1980) *Ann. Rev. Genet.* 14: 399–445. Several commercial manufacturers of molecular biology reagents sell prokaryotic expression vectors that have been optimized for high levels of heterologous gene expression [See, e.g., product catalogs from Stratagene Cloning Systems, La Jolla Calif.; Clontech Laboratories, Palo Alto Calif.; Promega Corporation, Madison Wis.]. These vectors are especially suitable for producing recombinant DPD, and are used as directed by the manufacturer, except that modifications to the growth medium are required for DPD expression, as described below.

Suitable expression vectors for use in prokaryotes typically contain a selectable marker that, when cells are grown under appropriate conditions, cause only those cells that contain the expression vector to grow. Examples of such markers useful in *E. coli* include genes specifying resistance to ampicillin, tetracycline, or chloramphenicol. See, e.g., Sambrook, supra. for details concerning selectable markers suitable for use in *E. coli*.

Overexpression of DPD causes elimination of pyrimidines from cells. This results in selection against cells that produce high levels of DPD. The present invention provides methods to circumvent this problem. These methods involve adding uracil to the growth medium. Addition of other cofactors such as FAD and FMN also has a beneficial effect, although not as great as for uracil addition. For expression of DPD in *E. coli*, for example, a preferred medium is Terrific Broth [Tartof and Hobbs (1987) Bethesda Research Labs FOCUS 9: 12] that contains 100 $\mu$g/ml ampicillin or other antibiotic suitable for the selectable marker contained on the expression vector employed. To allow growth of cells that express DPD, the medium is typically supplemented with 100 $\mu$M uracil, and optionally 100 $\mu$M each of FAD and FMN, and 10 $\mu$M each of Fe(NH$_4$)$_2$SO$_4$ and Na$_2$S.

Recombinant DPD produced by prokaryotic cells may not necessarily fold into the same configuration as eukaryotically-produced DPD. If improper folding inhibits DPD activity, one can "refold" the DPD polypeptide by first denaturing the protein, and then allowing the protein to renature. This can be accomplished by solubilizing the bacterially produced proteins in a chaotropic agent such as guanidine HCl, reducing all the cysteine residues by using a reducing agent such as $\beta$-mercaptoethanol. The protein is then renatured, either by slow dialysis or by gel filtration. See, e.g., U.S. Pat. No. 4,511,503.

Detection of the expressed antigen is achieved by methods known in the art as radioimmunoassay, or Western blotting techniques or immunoprecipitation. Purification from *E. coli* can be achieved following procedures described in, for example, U.S. Pat. No. 4,511,503.

3. Purification of DPD Polypeptides

The DPD polypeptides produced by recombinant DNA technology as described herein can be purified by standard techniques well known to those of skill in the art. Typically, the cells are lysed (e.g., by sonication) and the protein is then purified to substantial purity using standard techniques such as selective precipitation with such substances as ammonium sulfate, column chromatography, immunopurification methods, and others. See, e.g., R. Scopes, *Protein Purification: Principles and Practice*, Springer-Verlag: New York (1982), which is incorporated herein by reference. For example, one can raise antibodies against the DPD polypeptides and use the antibodies for immunoprecipitation or affinity chromatography using standard methods.

If the DPD polypeptide is produced as a fusion protein, in which the DPD moiety is fused to non-DPD amino acids, the desired polypeptide can be released by digestion with an appropriate proteolytic enzyme.

D. Use of DPD nucleic acids as selectable markers

Another aspect of the claimed invention is the use of a DPD nucleic acid as a selectable marker that is effective in both prokaryotes and eukaryotes. Selectable markers are genes that, when present in a cloning vector, produce a gene product that enables cells containing the vector to grow under conditions that prevent cells lacking the vector from growing. In contrast to the selectable markers of the invention, most selectable markers function only in one or the other of eukaryotes and prokaryotes, not in both. Thus, cloning vectors that are intended for propagation in both types of organisms usually require two different selectable markers.

The claimed selectable markers are DPD-encoding nucleic acids. Cells that express these nucleic acids are resistant to 5-FU. 5-fluorouracil, which is toxic to both prokaryotic and eukaryotic cells, is degradatively inactivated by DPD. Therefore, one can select cells that contain a DPD nucleic acid that is operably linked to a promoter simply by growing the cells in the presence of 5-FU. To practice the invention, one operably links the DPD nucleic acid to a promoter that functions in the host cell of interest. Suitable promoters and other control signals are described above. In a preferred embodiment, the DPD nucleic acid is integrated into an expression cassette that functions in both prokaryotes and eukaryotes. One example of such a bifunctional expression cassette is the ZAP Express™ expression cassette (Stratagene, La Jolla Calif.), which is described in U.S. Pat. No. 5,128,256. The DPD nucleic acid is inserted into the multiple cloning site which is downstream of a tandem array that includes both prokaryotic and eukaryotic transcription and translation regulatory sequences.

To determine appropriate growth conditions for using the DPD selectable marker, one first tests the untransformed host cells of interest for ability to grow in medium containing various amounts of 5-FU. A 5-FU concentration that results in complete or nearly complete inhibition of host cell growth is then employed in the medium used to select transformants. The amount of 5-FU required may vary depending on the particular medium used, the host cells, and whether the cells are grown in liquid culture or on a solid medium such as agar.

EXAMPLES

Example 1

Cloning and Characterization of Pig and Human DPD cDNAs

In this Example, we describe the cloning and characterization of cDNAs for pig and human dihydropyrimidine dehydrogenases.

MATERIALS AND METHODS

We isolated total RNA from frozen pig liver using the method of Chirgwin et al. (1979) *Biochemistry* 18: 5294–5299, except that we used CsTFA (Pharmacia, Inc., Milwaukee, Wis.) instead of CsCl. We extracted the RNA twice with phenol-chloroform emulsion and then ethanol precipitated the RNA prior to use. Next, we isolated poly(A) RNA by oligo (dT)-cellulose chromatography [Aviv and Leder (1977) *Proc. Nat'l. Acad. Sci. USA* 69: 1408–1412] and used it as a template for synthesis of cDNA. We used oligo-dT as a primer, and extended the primer using reverse transcriptase. Then, we made the cDNA double-stranded and cloned it into λgt24A using a kit supplied by Gibco BRL Life Technologies, Inc., Gaithersburg, Md. The DNA was packaged using the λ packaging system from Gibco BRL. We plated the phage particles in *Escherichia coli* Y1090r.

To identify plaques that express pig DPD, we screened the library using a polyclonal antibody against pig DPD [Podschun et al. (1989) *Eur. J. Biochem.* 185: 219–224]. We obtained a partial cDNA that we used to rescreen the library in *E. coli* Y1088 by plaque hybridization. This yielded a CDNA that contained the complete DPD reading frame. We subcloned the cDNA into the NotI and SalI sites of the plasmid vector pSport (Gibco BRL).

To clone the human DPD cDNA, we used a fragment of the pig cDNA that includes most of the coding region to screen previously amplified human liver cDNA libraries that had been prepared in λgt11 [Yamano et al. (1989) *Biochemistry* 28: 7340–7348]. We isolated the human DPD cDNA as three overlapping fragments, which we subcloned into the Eco RI site of pUC18. The three fragments were joined together using overlapping Cla I sites in pUC18. We then determined the complete sequences of pig and human DPD cDNAs using an Applied Biosystems 373A DNA sequencer, synthetic primers, and fluorescent dye terminator chemistry as described by the manufacturer. The oligonucleotide primers were synthesized using a CENTRICON 10™ filter (Millipore Corp.). Each base was determined at least once on both strands. The DNA and deduced amino acid sequences were analyzed using MacVector sequence analysis software (International Biotechnologies, Inc., New Haven, Conn.).

RESULTS

We isolated partial pig cDNAs by screening $1 \times 10^6$ plaques from an unamplified λgt22A library. After verification by sequencing, we used a partial cDNA to rescreen 500,000 plaques. Four cDNAs were isolated which contained inserts of about 4.5 kb. We completely sequenced one of these and found that it encompassed the full coding region of the protein (FIGS. 2A–2B). The deduced amino acid sequence of the amino terminal region agrees with the amino acid sequence determined from the pig enzyme [Podschun et al. (1989) *Eur. J. Biochem.* 185: 219–224]. A number of segments of amino acids previously sequenced were found in the cDNA-deduced amino acid sequence (FIG. 3, underlined). These were determined by cyanogen bromide cleavage (residues 117–127) and trypsin cleavage (residues 260–277; 308–315; 656–682; 904–913) followed by HPLC separation and sequencing (data not shown). The first residue of the amino terminal portion of the 12,000 dalton cleavage fragment from the pig DPD is shown by a vertical arrow at residue 904. These data establish the pig DPD open reading frame of 1025 amino acids.

The nucleotide sequence of the human DPD is shown in FIGS. 1A–1B. The deduced amino acid sequence of the human DPD is identical to that of the pig DPD, except where indicated in FIG. 3. The calculated molecular weights are 11,416 and 111,398 daltons for pig and human DPD, respectively. The poly(A) addition sequence of AAATAAA is found 17 bp upstream of a putative poly(A) tract cloned in the cDNA. This 3'-untranslated region was not isolated in the human cDNA clones.

The cDNA-derived protein sequences revealed the presence of a number of putative binding sites for known DPD cofactors. Recent EPR measurements on DPD from *Alcaligenes eutrophus* confirmed the existence of FMN, iron, and acid-labile sulfide, the latter two of which are indicative of iron sulfur clusters [Schmitt et al. (1994) *J. Inorg. Biochem.* (in press). The C-terminal 12 kDa peptide fragment purified from the pig DPD shows absorbance in the 500–600 nm region and contains eight iron and eight acid-labile sulfides (Podschun et al. (1989), supra.]. The binding site of iron-sulfur clusters contain Cys residues, a large number of which are found in the N-terminal half of the protein. However, these do not exhibit the typical motif pattern seen in other well-characterized iron sulfur-containing proteins. In the C-terminal region of pig and human DPD are typical motifs CXXCXXCXXXCX (SEQ ID No. 11) and CXXCXX-CXXXCP (SEQ ID No. 12) for [4Fe-4S] clusters [Dupuis et al. (1991) *Biochemistry* 30: 2954–2960] between residues 953 and 964 and residues 986 and 997, respectively. These lie within the 12 kDa iron-sulfur cluster-containing peptide [Podschun et al. (1989), supra.]. No other [4Fe-4S] clusters were detected; however, other types of iron sulfur clusters such as [2Fe-2S] might be possible.

A typical NADPH binding motif VXVXGXGXXGXXX-AXXA (SEQ ID No. 13) [Wierenga et al. (1985) *Biochemistry* 24: 1346–1357] begins with V-335, except that the Gly at position 10 is an Ala in pig and human DPD. A motif for FAD binding, TXXXXVFAXGD [Eggink et al. (1990) *J. Mol. Biol.* 212: 135–142], is in the N-terminal region starting with T-471 and ending with D-481.

We elucidated the putative uracil binding site of DPD by incubating DPD in the presence of 5-iodouracil, a suicide inactivator of the bovine enzyme, and sequencing the modified chymotryptic peptide [Porter et al. (1991) *J. Biol. Chem.* 266: 19988–19994]. The corresponding sequence obtained is located between G-661 and R-678 in the primary protein sequence. Thus, the order of the functional domains of DPD is, from the N-terminus, NADPH/NADP-FAD-uracil-[4Fe-4S].

Example 2

Chromosome localization of the DPD gene

We localized the DPD gene to a specific human chromosome using a somatic cell hybrid strategy. Human-mouse and human-hamster cell lines were generated and characterized as described by McBride et al. [(1982a) *Nucl. Acids Res.* 10: 8155–8170; (1982b) *J. Exp. Med.* 155: 1480–1490; (1982c) *Proc. Nat'l. Acad. Sci. USA* 83: 130–134]. The human chromosome of each call line was determined by standard isoenzyme analyses as well as by Southern analysis with probes from previously localized genes, and frequently, by cytogenetic analysis. Southern blots of hybrid cell DNA restriction digests on positively charged nylon membranes were prepared after (0.7%) agarose gel electrophoresis and hybridized at high stringency with $^{32}$P-labeled probes under conditions allowing no more than 10% divergence of hybridizing sequences.

We localized the DPD gene to human chromosome 1 by Southern analysis of a panel of human/rodent somatic cell hybrid DNAs digested with Eco RI using a 3' coding cDNA fragment as probe (Table 1). The gene segregated discordantly ($\geq$14%) with all other human chromosomes. The 3' probe identified a series of bands in human DNAs ranging in size from 0.8 to 1.5 kb. All hybridizing human bands appeared to cosegregate indicating that these bands were all present on the same chromosome. We then sub-localized the gene on chromosome 1 by analysis of hybrids containing spontaneous breaks and translocations involving this chromosome. One human/hamster hybrid with a break between NRAS (1p12) and PGM1 (1p22) retained the telomeric portion of the chromosome 1 short arm but the DPD gene was absent from this hybrid. Another human/hamster hybrid and a human/mouse hybrid each retained all, or nearly all, of the short arm of chromosome 1 including NRAS and all other short arm markers but all long arm markers were absent including a cluster of genes at 1q21 (trichohyalin, loricrin, and filaggrin); the human DPD gene was present in both of these hybrids. Finally, one additional human/hamster hybrid retained a centromeric fragment of chromosome 1 with the breakpoints on the long arm and short arm proximal to 1q21 and proximal to 1p31, respectively, and human DPD was present in this hybrid. These results indicate that the DPD gene can be sublocalized to the region 1p22-q21.

We confirmed these results by Southern analysis of the same panel of hybrids with a DPD 5' cDNA probe which detected 1.5, 5.0, 8.7, and 11.6 kb bands in human EcoRI digests. Both probes were used to examine DNAs from ten unrelated individuals separately digested with 12 different restriction enzymes for RFLPs. However, no polymorphisms were detected. A large number of hybridizing bands were detected with both DPD probes and these bands cosegregated indicating that they are all localized to the centromeric region of human chromosome 1 (i.e., 1p22-q21). A number of cross-hybridizing hamster and mouse bands were also identified with these probes. These results are consistent with the interpretation that there may be a single reasonably large gene (spanning at least 80 kb) in each of these species, and all hybridizing bands arise from a single gene. However, we currently cannot exclude the possibility that the many hybridizing bands arise from a cluster of tandemly linked genes.

Recently, the human DPD gene (named "DPYD" by the human gene nomenclature committee) was more precisely mapped to 1p22 [Takai et al. (1994) (submitted for publication)].

Example 3

Expression of Pig DPD in *E. coli*

In this Example, we demonstrate the heterologous expression of a DPD polypeptide in a prokaryotic organism. Because large amounts of DPD protein are toxic to the host cells under normal growth conditions, additional components such as uracil are required in the medium.

METHODS

Construction of the Expression Plasmid. We constructed an expression plasmid by subcloning the pig DPD cDNA into the vector pSE420 (Invitrogen Corp., San Diego, Calif.). The cDNA contains an Nco I site coincident with the start codon (CCATGG) which was joined to the Nco I site in the vector that is in frame with the bacterial initiator Met. The pig DPD cDNA was inserted into pSE420 as an NcoI/AflIII fragment from the pSPORT vector in which the pig DPD cDNA had previously been subcloned.

DPD Expression in *Escherichia coli*. For each expression experiment, a single colony from a freshly made transformation of DH-5α cells with the expression vector was inoculated in LB broth and grown to stationary phase. An aliquot from this culture was used to inoculate 250 ml of terrific broth containing 100 μg/ml ampicillin and supplemented with 100 μM of each FAD and FMN, 100 μM uracil and 10 μM each of $Fe(NH_4)_2(SO_4)$ and $Na_2S$. Following a 90 min incubation at 29° C., we induced the trp-lac promoter in the expression vector by the addition of 1 mM isopropyl-β-d-thiogalacto-pyranoside (IPTG) and the culture was incubated for an additional 48 h.

The cells were then sedimented, washed twice with 250 ml of phosphate buffered saline (PBS) and resuspended in 45 ml of 35 mM potassium phosphate buffer (pH 7.3) containing 20% glycerol, 10 mM EDTA, 1 mM DTT, 0.1 mM PMSF and 2 μM leupeptin. The cell suspension was lysed at 4° C. with four 30 sec bursts of a Heat Systems sonicator model W 225-R at 25% of full power (Heat Systems-Ultrasonics, Inc., Plain View N.Y.). The resultant lysate was centrifuged at 100,000×g for 60 min at 4° C. We then slowly added solid $(NH_4)_2SO_4$ to the supernatant at 4° C. with gentle stirring to give a final concentration of 30% saturation. The precipitate was sedimented and the pellet containing expressed DPD was resuspended in 5 ml of 35 mM potassium phosphate buffer (pH=7.3) containing 1 mM EDTA/1 mM DTT and 0.1 mM PMSF. The protein solution was dialyzed at 4° C. for 36 h against 3 changes of 4 liters each of buffer and stored at −70° C. until further use.

Catalytic assay. DPD activity was determined at 37° C. by measuring the decrease in absorbance at 340 nm associated with the oxidation of NADPH to $NADP^+$. The reaction mixture contained 28 mM potassium phosphate buffer (pH 7.3), 2 mM $MgCl_2$, 1 mM DTT, 60 μM NADPH and the expressed DPD in a final volume of 1 ml. The measurements were carried out using an Aminco DW-2000 double beam spectrophotometer using a blank that contained the complete reaction mixture except substrate. The reactions were initiated by addition of substrate (uracil, 5-fluorouracil or thymine). The catalytic activity was calculated as μmole of NADPH oxidized per minute and per mg of expressed DPD. Protein quantities were determined using the bicinchronic (BCA) procedure from Pierce Chemical Co., Rockford, Ill.) following the manufacturer's directions.

Analysis of cDNA-Expressed DPD Protein. SDS-polyacrylamide gel electrophoresis was carried out following the method of Laemmli [(1970) *Nature* 227: 680–685] using 8% acrylamide slab gels. The SDS-page gels were transferred to a nitrocellulose membrane by electroblotting for 90 min at 1.5 mA/cm$^2$ [Towbin et al. (1979) *Proc. Nat'l Acad. Sci. USA* 76: 4350–4354]. The membranes were blocked at room temperature using phosphate buffered saline (PBS) containing 0.5% Tween 20 and 3% skim milk. After blocking, the membranes were incubated for 4 h at room temperature with rabbit anti pig DPD polyclonal antibody dilute 200-fold in PBS. The membranes were washed three times in PBS containing 0.5% Tween 20 and rinsed twice with PBS prior to addition of alkaline phosphatase-labeled goat anti-rabbit IgG. Incubation was continued for 90 min and the membranes were developed using the reagent BCIP/NBT (Kikegaard & Perry Labs. Gaithersburg, Md.).

RESULTS

The pig DPD was expressed in bacteria using the vector pSE 420 which has a trp-lac promoter that is inducible by isopropyl-β-d-thiogalacto-pyranoside (IPTG). Optimal expression was obtained when cells were grown at a temperature between 26° C. and 30° C. Growth at higher temperatures resulted in aggregation of the protein in inclusion bodies. A number of cofactors known to be associated with the enzyme were added to the medium; the most critical was uracil which resulted in a greater than five-fold increase in DPD expression levels, compared to cells grown in unsupplemented medium.

The recombinantly expressed DPD enzyme comigrated with the intact 102 kDa DPD purified from pig liver and reacted with rabbit polyclonal antibody [Podschun et al. (1989) supra.] directed against the pig enzyme. DPD protein was undetectable in cells containing the expression vector without the DPD cDNA insert. The DPD purified from pig liver frequently has a second higher mobility band of about 12 kDa that results from a protease-labile site that liberates the iron sulfur-containing C-terminal fragment [Podschun et al. (1989) supra.].

The bacterially-expressed enzyme is produced intact and could be significantly purified away from other *E. coli* proteins by a single ammonium sulfate fractionation. By use of the purified pig DPD as a standard, we estimate that 50 to 100 mg of DPD were produced per liter of *E. coli* culture.

We tested the recombinantly expressed DPD enzyme for ability to metabolize typical DPD substrates such as uracil, thymine and 5-fluorouracil. Kinetic studies revealed that the recombinant DPD follows the ping pong reaction mechanism as previously shown for purified pig DPD [Podschun et al. (1989), supra.]. The Km's of the recombinant DPD are of similar magnitude to the values published for the purified pig [Podschun et al. (1989), supra.], human [Lu et al. (1992) *J. Biol. Chem.* 267: 17102–17109] and rat DPD enzymes [Fujimoto et al. (1991) *J. Nutr. Sci. Vitaminol.* 37: 89–98]. The Vmax values of expressed DPD were about three to five-fold lower than the purified pig enzyme reflecting the fact that the expressed DPD was only partially purified. However, these data establish that the expressed enzyme reflects the properties of the purified pig liver DPD. Thus, *E. coli* should prove useful for examining any enzymatic variants obtained through screening DPD-deficient individuals and for preparing large amounts of intact holoenzyme for physico-chemical analysis.

Example 4

Identification of Mutations Within DPYD Gene

In an effort to understand the genetic basis for DPD deficiency, we analyzed a Dutch family that included a DPD-deficient individual. We determined the phenotype for thymine metabolism and related it to the DPD protein content in fibroblasts. Then we identified the genetic defect using RT-PCR and found that the deficiency was due to a homozygous deletion in the DPD mRNA. The deleted portion corresponded to an exon in the DPYD gene. This phenotype/genotype relationship accounts for the DPD metabolic disorder in the patient. Additionally, we confirmed an autosomal recessive pattern of inheritance for DPD deficiency.

METHODS

Isolation of RNA. RNA was isolated from cultures of human fibroblast corresponding to all five subjects used in this study by the guanidinium thiocyanate phenol-chloroform method [Chomczynski and Sacchi (1987) *Anal. Biochem.* 162: 156–159]. The RNA was dissolved in water and stored at −80° C. until further use.

RT-PCR. cDNA was synthesized by reverse transcription from total RNA isolated from cultured fibroblast. About 1 μg of total RNA was mixed with oligo-dT primers and incubated at 65° C. for 15 min to denature secondary structure in the template. The primed RNA was incubated for 60 min at 40° C. in 20 μl of a reaction mixture containing 100 mM Tris-HCl (pH 8.3), 40 mM KCl, 10 mM $MgCl_2$, 50 μM spermidine, 100 mM dNTPs, 4 mM sodium phosphate, 0.5 units placental RNase inhibitor and 0.5 units of AMV reverse transcriptase (Invitrogen, Calif.). The synthesis reaction was repeated once by the addition of 0.5 units of fresh reverse transcriptase. The cDNA was made double stranded by PCR without further purification. The coding region of the cDNA was amplified in three fragment with the primer pairs indicated in Table 1.

TABLE 1

Primer pairs for RT-PCR analysis of human DPD CDNA (hDPD).

| Fragment amplified | Location in hDPD cDNA (nucleotides) | Primer sequence | SEQ. ID No. |
|---|---|---|---|
| 1.5 kb | RTF1.36–55 | 5'GCAAGGAGGGTTTGTCACTG3' | 5 |
|  | RTR1:1558–1536 | 5'CCGATTCCACTGTAGTGTTAGCC3' | 6 |
| 906 bp | H13:1539–1558 | 5'TAACACTACAGTGGAATCGG3' | 7 |
|  | RTR4:2445–2426 | 5'AAATCCAGGCAGAGCACGAG3' | 8 |
| 919 bp | RTR5:2424–2447 | 5'TGCTCGTGCTCTGCCTGGATTTCC3' | 9 |
|  | RTR5:3343–3320 | 5'ATTGAATGGTCATTGACATGAGAC3' | 10 |

We carried out PCR in 50 μl of a reaction mixture consisting of 10 mM Tris-HCl (pH 8.3), 50 mM KCl, 2.5 mM $MgCl_2$, 0.5 mM dNTPs, 1 μM primers and 2.5 units Taq polymerase (Perkin-Elmer Cetus). Thirty cycles were used, each cycle consisted of denaturing at 96° C. for 1 min, annealing at 55° C. for 1 min and extending at 72° C. for 2 min. The amplified products were extracted with 1 volume chloroform and purified by filtration through Centricon™ 100 filter units (Amicon, Inc. Beverly Wash.). Typically, we used one fifth of the PCR product for DNA sequence analyses with an Applied Biosystems 373A automated sequencer and fluorescent dye-deoxy terminator chemistry. We elucidated appropriate primers for DNA sequencing from the DPD cDNA sequence disclosed herein and synthesized the primers using an Applied Biosystems 394 DNA & RNA synthesizer. Sequence data have been analyzed using MacVector™ sequence analysis software (International Biotechnologies).

PCR Product Analysis and Southern Blots. We analyzed the PCR fragments by electrophoresis through a 1% agarose gel in the presence of ethidium bromide. Prior to Southern blotting, the gels were depurinated by a 20 min incubation in 200 mM HCl, after which we denatured the DNA by a 20 min incubation in 0.5 M NaOH. The DNA was transferred to Gene Screen Plus™ membranes (New England Biolabs) overnight in 0.5 M NaOH as the transfer solution. We fixed the DNA by baking at 80° C., prehybridized at 65° C. for 3 h in a solution containing 6× SSC, 1× Denhardt's reagent, 0.5% sodium dodecyl sulfate and 0.2 mg/ml sonicated salmon sperm DNA. We then hybridized overnight at 65° C. in the same solution containing $1.5 \times 10^6$ cpm/ml of $^{32}$P random priming labelled human DPD cDNA. After washing at 65° C. for 20 min in 2× SSC, 0.5% SDS and 45 min 0.1× SSC, 0.5% SDS at 65° C., the membranes were exposed to X-ray film (Eastman Kodak, Co.) at −80° C. for 30 min.

Western Immunoblots. We carried out SDS-PAGE gel electrophoresis using the method of Laemmli (1970) *Nature* 227: 107–111. The gels were transferred to nitrocellulose by semi-dry electroblotting for 90 min at 1.5 mA/cm$^2$. We detected DPD polypeptides using rabbit anti-pig DPD primary antibody and the enhanced chemiluminescence (ECL) detection method (Amersham Corp.), following the directions supplied by the manufacturer. Protein concentrations were determined using the bicinchronic acid procedure (Pierce Chemical Co., Rockford, Ill.) using bovine serum albumin as standard.

Catalytic Activity. We measured DPD activity in human fibroblast extracts by HPLC using a modification of the method described by Tuchman et al. (1989) *Enzyme* 42: 15–24, using [$^{14}$C]-thymine as substrate.

RESULTS

Clinical evaluation. We have studied the genetic basis for the complete lack of DPD activity in one of the members of the pedigree shown in FIG. 4. The patient (subject 4) was admitted to the hospital at the age of 25 months with bilateral microphtalmia, iris and choroidea coloboma, and nystagmus, in addition to a gradually increasing psychomotor retardation. However, no growth retardation or neurological abnormalities were detected. All other members of the pedigree were healthy and showed no abnormalities. The patient was diagnosed to have severe thymine-uraciluria. Skin biopsies were taken in order to establish fibroblast cultures that were used in this study.

Figure 7:
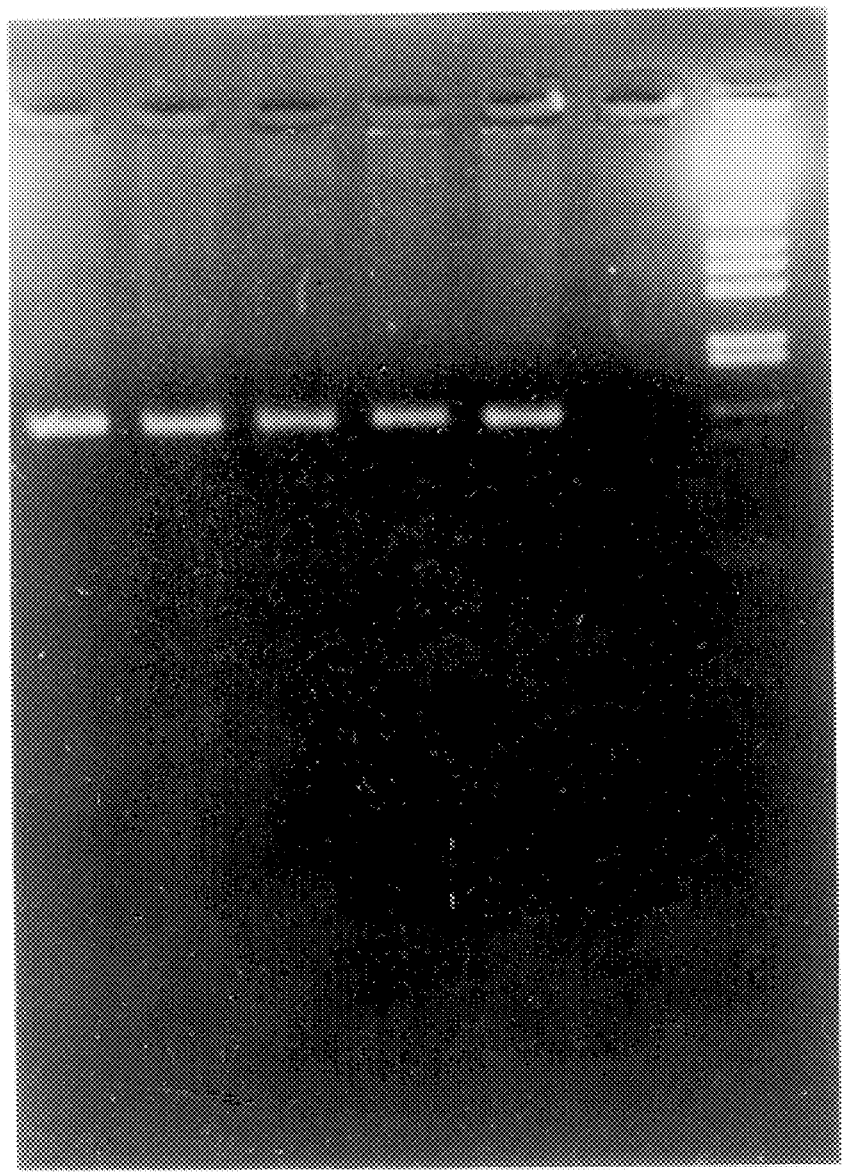
FIG. 7 is a PCR analysis of the DPD cDNA deletion found in the subject family. The numbers of the subjects correspond to those indicated in FIG. 4. Lane 6 is a negative control (no template present) and Lane 7 contains a 1 kb marker ladder (GIBCO BRL).

RT-PCR analysis of the DPD mRNA in cultured fibroblasts. Fibroblast total RNA from every subject was subjected to RT-PCR. The PCR products were hybridized with the [$^{32}$P]-labelled human DPD cDNA and the result is shown in FIG. 5. The coding sequence of the DPD cDNA was fully amplified in three fragments that span 1500, 906 and 919 bp. All the fragments are present every subject, including the patient. The 1500 and 919 bp fragments were constant in all subjects. However, the 906 bp fragment was found in only certain subjects and was in linkage disequilibrium with a fragment of 741 bp. The latter was homozygous in the deficient patient and found together with the predicted normal size fragment in both parents. One sibling was heterozygous and another was homozygous for the normal allele. To confirm the possibility of a deletion in the mRNA-derived cDNA associated with the DPYD alleles of these subjects, we sequenced the PCR fragments using nested primers and found that the 741 originated from the 906 bp fragment by a deletion of 165 bp. A schematic representation showing the structure of both mRNAs is shown in FIG. 6. Through partial sequencing of the DPYD gene, we found that the deletion present in the mRNA was coincident with a splicing site located in the genomic sequence of the DPYD gene that comprises a 165 bp exon. We have also found that the DNA corresponding to the deletion is present in the genomic DNA from the fibroblast cell lines since, as shown in FIG. 7, the deleted cDNA sequence can be amplified by PCR from the genomic DNA in the patient, as well as from genomic DNA from other members of the family. These results indicate that the variant transcript is not the result of a large deletion containing the missing exon, but rather is the result of a mutation that causes incorrect splicing.

Catalytic activity and DPD protein content. DPD activities from the fibroblast cell lines were determined by HPLC (Table I). The maximum activity, 1 nmol h$^{-1}$, mg protein$^{-1}$, corresponds to subject 3 that was homozygous for the normal mRNA. The parents and another sibling (subjects 4, 5, and 2) present a lower value and the patient, subject 1, had background activity. It should be noted that the DPD activity obtained in human fibroblast is about 8–9 times lower than the equivalent activity in DPD from human lymphocytes.

To determine if the DPD protein content in our subjects follows a pattern similar to that of the catalytic activity, we measured fibroblast DPD protein by Western blots. DPD protein was not detectable in the patient, but was found in two other members of his family (subjects 2 and 4 in FIG. 4) who were analyzed for comparison.

The catalytic activity pattern correlates with the DPD protein content for the different subjects. As expected, the patient with only background DPD activity in his fibroblast has no detectable DPD band in the Western blot when using an anti-pig DPD polyclonal antibody, suggesting a complete lack of DPD protein. It is interesting to note that even though the DPD protein is defective and does not accumulate in the cell, the DPD mRNA is present, indicating that the defective mRNA is not particularly unstable as compared to the mRNA encoding the active DPD protein.

In conclusion, this study established with certainty that thymine uraciluria is due to a mutation in the DPYD gene.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated by reference.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for determining whether a patient is at risk of a toxic reaction to 5-fluorouracil, the method comprising analyzing DPD DNA or mRNA in a sample from the patient, using a nucleic acid probe selected from the group that consists of SEQ ID NO:1, a specific subsequence thereof, SEQ ID NO:3, a specific subsequence thereof, and nucleic acid probes that selectively hybridize under stringent conditions to SEQ ID NO:1, to a specific subsequence thereof, to SEQ ID NO:3, to a specific subsequence thereof, and complementary sequences of all of the above, to determine the amount of intact DPD nucleic acid in the sample, wherein an enhanced risk of a toxic reaction to 5-fluorouracil is indicated by a decrease in the amount of intact DPD DNA or mRNA in the sample compared to the amount of DPD DNA or mRNA in a sample obtained from a patient known to not have a DPD deficiency.

2. A method of claim 1 wherein an enhanced risk of a toxic reaction is indicated by a decrease of greater than about 70%.

3. A method of claim 1 wherein an increased risk of a toxic reaction is indicated by a decrease of greater than about 50%.

4. The method of claim 1, wherein the method comprises the steps of:

(a) obtaining a cellular sample from the patient;

(b) extracting DNA or RNA from the sample;

(c) hybridizing a probe comprising a DPD nucleic acid to the DNA or RNA from the sample; and (d) determining whether the DPD nucleic acid binds to the DNA or RNA.

5. The method of claim 1, wherein the DPD nucleic acid is analyzed by RT-PCR.

6. The method of claim 1, wherein the DPD nucleic acid is analyzed by PCR sequencing of genomic DNA from the patient.

7. A method of claim 1 wherein the cellular sample comprises lymphocytes.

8. A method for determining whether a patient is at risk of a toxic reaction to 5-fluorouracil, the method comprising analyzing DPD DNA or mRNA in a sample from the patient to determine the amount of intact DPD nucleic acid, wherein an enhanced risk of a toxic reaction to 5-fluorouracil is indicated by a decrease in the amount of intact DPD DNA or mRNA in the sample compared to the amount of DPD DNA or mRNA in a sample obtained from a patient known to not have a DPD deficiency, wherein the probe oligonucleotide probe that is capable of selectively hybridizing, under stringent hybridizing conditions, to a DPD nucleic acid having a nucleotide sequence or a specific subsequence of that shown in Seq. ID No. 1 or Seq. ID No. 3.

9. A method of claim 8 wherein the oligonucleotide probe is between about 10 and 100 nucleotides in length.

* * * * *